US012702305B2

(12) United States Patent
Lim

(10) Patent No.: US 12,702,305 B2
(45) Date of Patent: Aug. 11, 2026

(54) SKIN EXAMINATION DEVICE

(71) Applicant: MACQUARIE MEDICAL SYSTEMS PTY LTD, Leichhardt (AU)

(72) Inventor: Kar Gay Lim, Botany (AU)

(73) Assignee: MACQUARIE MEDICAL SYSTEMS PTY LTD, Leichhardt (AU)

( * ) Notice: Subject to any disclaimer, the term of this patent is extended or adjusted under 35 U.S.C. 154(b) by 0 days.

(21) Appl. No.: 18/686,293

(22) PCT Filed: Aug. 24, 2022

(86) PCT No.: PCT/AU2022/050980

§ 371 (c)(1),
(2) Date: Feb. 23, 2024

(87) PCT Pub. No.: WO2023/023753

PCT Pub. Date: Mar. 2, 2023

(65) Prior Publication Data

US 2025/0152012 A1 May 15, 2025

(30) Foreign Application Priority Data

Aug. 24, 2021 (AU) ................................ 2021107649
Aug. 24, 2021 (AU) ................................ 2021221543
Aug. 24, 2021 (AU) ................................ 2021902688

(51) Int. Cl.
*A61B 5/00* (2006.01)

(52) U.S. Cl.
CPC ............ *A61B 5/0079* (2013.01); *A61B 5/004* (2013.01); *A61B 5/0077* (2013.01); *A61B 5/444* (2013.01); *A61B 2560/0431* (2013.01)

(58) Field of Classification Search
CPC ..... A61B 5/0079; A61B 5/004; A61B 5/0077; A61B 5/444; A61B 5/445;
(Continued)

(56) References Cited

U.S. PATENT DOCUMENTS 6,032,071 A * 2/2000 Binder ................ A61B 5/6844
356/369
2001/0004513 A1* 6/2001 Chang ................. G02B 5/0268
430/394

(Continued)

OTHER PUBLICATIONS

Wang, Hening, et al. "Systematic design of a cross-polarized dermoscope for visual inspection and digital imaging." IEEE instrumentation & measurement magazine 14.6 (2011): 26-31. (Year: 2011).*

(Continued)

*Primary Examiner* — Sean D Mattson
(74) *Attorney, Agent, or Firm* — Heslin Rothenberg Farley & Mesiti P.C.; Jacquelyn A. Graff, Esq.

(57) ABSTRACT

A device for examination of a skin site is disclosed comprising a housing, an illumination module arranged within the housing, and operable for emitting and dispersing light. The device further comprises an imaging module arranged within the housing, a lens of the liquid lens type arranged in operable association with the imaging module, and a distortion correction lens. The device is configured operable so that in use (i) light is radiated from the illumination module for projection on to the skin site in a radiated light path; and (ii) light is reflected from the skin site to the imaging module in a reflected light path. The distortion correction lens is arranged in the reflected light path between the skin site and the liquid lens.

22 Claims, 11 Drawing Sheets

(58) Field of Classification Search

CPC ............ A61B 2560/0431; G01J 1/0233; G01J 1/0271; G01J 1/0429; G01J 1/0474; G01J 1/08; G01J 1/0204; G01J 1/0422; G01J 2001/0481; G01J 2001/0257; G01J 2003/104; G01J 3/0205; G01J 3/0224; G01J 3/0272; G01J 3/0291; G01J 3/10; G02B 5/0284; G02B 27/022; G02B 27/02; G01N 21/474; G01N 21/21; G01N 21/47; G01N 2021/4754; G03B 2215/0567; G03B 2215/0575; G03B 21/12; G06T 2207/30088

See application file for complete search history.

(56) References Cited

U.S. PATENT DOCUMENTS

2009/0263040 A1 10/2009 Rolland et al.
2012/0044682 A1 2/2012 Allen et al.
2014/0303505 A1* 10/2014 Toriumi ............... A61B 5/0079 600/476
2015/0009649 A1 1/2015 Jagt et al.
2015/0036311 A1 2/2015 Mullani
2015/0199819 A1* 7/2015 Suzuki ................. A61B 5/0037 382/164
2016/0296119 A1* 10/2016 Nakamura ........... A61B 5/0075
2018/0279942 A1* 10/2018 Houjou ................ A61B 5/0064
2019/0090751 A1 3/2019 Hwang et al.
2019/0343396 A1 11/2019 Khosravi Simchi et al.
2019/0343450 A1 11/2019 Park
2019/0350513 A1* 11/2019 Carrein ................ A61B 5/0077
2019/0387958 A1 12/2019 Kimpe et al.
2021/0137633 A1* 5/2021 Mullani ................. A61B 5/441

OTHER PUBLICATIONS

Ugarte, M. F., et al. “Active multispectral imaging system for photodiagnosis and personalized phototherapies.” Review of Scientific Instruments 85.10 (2014). (Year: 2014).*

Fricke Dierk et al: “Non-Contact Dermatoscope with Ultra-Bright Light Source and Liquid Lens-Based Autofocus Function”, Applied Sciences, May28, 2019, p. 2177, vol. 9, No. 11.

Yang Cheng et al: “Optical zoom imaging systems using adaptive liquid lenses”, Bioinspiration & Biomimetics, Institute of Physics Publishing, Bristol, GB, Jun. 22, 2021, p. 41002, vol. 16, No. 4.

Brandon Alan: “Samsung files patent for liquid zoom lens”, New Atlas, Nov. 7, 2010, pp. 1-4.

Extended European Search Report for European Application No. 228596409, Jan. 16, 2025, 12 pages.

International Search Report & Written Opinion of International Application No. PCT/AU2022/050980, Nov. 28, 2022, 19 pages.

International Preliminary Report on Patentability of International Application No. PCT/AU2022/050980, Oct. 30, 2023, 15 pages.

First Office Action for European Patent Application No. 22859640.9, March 10, 2026, 8 pages.

* cited by examiner

SKIN EXAMINATION DEVICE

CROSS REFERENCES TO RELATED APPLICATIONS

This application is a national stage filing under section 371 of International Application No. PCT/AU2022/050980 filed on Aug. 24, 2022, and published on Mar. 2, 2023 as International Publication No. WO 2023/023753, which claims priority to Australian Patent Application No. 2021107649 filed on Aug. 24, 2021, and Australian Patent Application No. 2021221543 file on Aug. 24, 2021, and Australian Patent Application No. 2021902688 filed on Aug. 24, 2021, the entire contents of each application are incorporated herein by reference in their entireties.

FIELD OF THE INVENTION

In one aspect, a skin examination device is disclosed. In another aspect, an illumination arrangement for use in a skin examination device is disclosed. In a further aspect, an optical arrangement for use in a skin examination device is disclosed. Related methods are also disclosed.

RELATED APPLICATIONS

The present application claims priority to Australian provisional patent application No. 2021902688 (AU'688) filed 24 Aug. 2021, and Australian patent application No. 2021221543 (AU'543) filed 24 Aug. 2021 (subsequently converted to Australian Innovation Patent No. 2021107649 (AU'649)). The contents of AU'688, AU'543 and AU'649 are incorporated herein by reference in their entireties.

BACKGROUND

Skin is a vital organ of the human body and often requires examination for disease and damage. In particular, melanoma (skin cancer) is a high-risk disease that can spread rapidly to other organs if it is not identified and diagnosed at an early stage.

According to official Australian government organisation, Cancer Australia, melanoma was the third most commonly diagnosed cancer in 2020 and at least two in three Australians are likely to be diagnosed with skin cancer before the age of 70. Similarly, according to Skin Cancer Foundation of America, it is estimated that about 207,390 cases will be diagnosed in the USA in 2021, and about 7,180 (~4,600 male, ~2,580 female) are likely to die of melanoma in 2021.

The standard method of detecting skin diseases, such as melanoma, is usually a physical examination, followed by biopsy when a particular area of the skin is determined to be suspicious by the examining medical doctor. The usual instruments used by doctors for a physical skin examination are handheld magnifying instruments known as dermatoscopes. Additionally, epiluminescence microscopy (ELM) of pigmented lesions of the skin is nowadays a well-established method for the early detection of skin cancer, and also for the differential diagnosis of pigmented skin lesions.

The human skin has an oily surface that reflects light. When taking images of the skin with traditional illuminating devices, the reflection of light by an oily surface will generally obscure the cells' structures underneath in the final image. An existing traditional method of reducing this reflection, called the oil immersion method, involves applying oils on to the skin and pressing a glass surface to the surface of the skin. This method can usually produce good images except in situations where the use of oil immersion method is neither suitable nor useful. For example, wounds and significantly curved areas of skin.

Existing in the art is a handheld skin examination device described in Australian patent AU 199538975 (AU'975) (and the associated patent family). The technology described in AU'975 utilises cross polarisation of light. Broadly, an illuminating light source is filtered by a linear polariser so that the incident light source is polarised in one fixed angle. As the light enters the skin, it gets dispersed inside the epidermal layer and changes the angle of polarisation. The light that is reflected off or from the skin will directly be filtered by a second polariser which is aligned generally perpendicular to the first polariser. An on-board imaging system operates to detect only those images beneath the reflective layer of the skin.

The 'cross polarisation' illumination method may be considered to have the following disadvantages:

- Illuminations and image quality—A typical linear polariser filters up to about 75% of the light passing through. Thus, the cross-polarisation method requires very a high intensity of light source in order to be effective as the amount of light that finally passes through to the on-board imaging system/camera is less than about 10% of the original intensity. This can result in low contrasts and shadowy imaging because of light absorption within the epidermal layer. As a result, some conditions of the skin may not be fully captured often causing biopsies to be prescribed to confirm the skin condition. Therefore, some doctors still use the traditional oil immersion method as the resulting images tend to be brighter and higher in contrast.
- Depth of field of focus in the skin layers—The device of AU'975 uses long focal length lenses and has a limited depth of field of around 0.2 mm. The software controlling the camera needs to shift the focus control to 0.2 mm into the skin in order to avoid focusing on the epidermal layer. This has been found to be insufficient to fully cover the depth required to identify structures underneath the 0.2 mm layer. As with typical camera lenses, the depth of field can be controlled by the aperture F-stop of the camera. The smaller the aperture, the larger the depth of field. However, due to the heavy loss of light, it is usually not practical to use a smaller aperture camera to increase the depth of field.
- Further, the type of video camera used also means the focus field is not flat, so the software controlling the camera operation needs to zoom in further to remove the blurry corners of the actual images. In order to provide different magnifications for different skin conditions, additional adapters are required to provide the user with the capability to attain 30×, 50×, and 80× magnification.
- Resolutions and colour quality—Due to the use of older analogue video image capturing hardware, the colour spectrum coverage of the signal is lossy and some colours are not fully reproduced after the analogue to digital conversion process. This usually means the type of display monitors used by a user will require more vivid display characteristics to match the PAL or NTSC colour spectrum. Most laptop LCD displays tend to produce dull images thus making diagnosis more difficult.

It is therefore against this general background that the principles described herein have been developed, and which seek to overcome or ameliorate, at least in part, the aforementioned disadvantages of previous or existing skin examination devices/technologies.

SUMMARY

According to a first aspect, there is provided an illumination arrangement for use with a device operable for use in the examination of a skin site, the illumination arrangement comprising:

- a reflector means or module having a reflecting portion configured operable for reflecting light received thereby,
- a light emitting means or module arranged between the reflector means or module and the skin site, and arranged operable with the reflector means or module so that a portion of light emitted from the light emitting means or module meets or makes contact with the reflecting portion of the reflector means or module, which meeting or contact is configured operable so as to promote scattering or diffusion of light for reflection from the reflecting portion of the reflector means or module for projection on to the skin site for increasing the variability or non-uniformity of incidence of the reflected scattered/diffused light received across the skin site.

In one embodiment, the increase in the variability or non-uniformity of incidence of the reflected scattered/diffused light received across the skin site operates to promote distribution or spread of the received light sub-surface of the skin site. In this manner, with the reflected scattered/diffused light entering the skin of the skin site, the sub-surface structure becomes brighter. This can have advantage in situations where the surface of the skin is oily.

In the context of the present principles described herein, the phrase 'incidence' of the reflected scatter/diffused light is a reference to the angle which an incident line a light ray makes with a perpendicular to the surface at the point of incidence. In the present context, the scattering/diffusion of the reflected light (rays) causes multiple light rays to be received by the skin site each at different angles of incidence, thereby increasing the variability or non-uniformity of incidence of the reflected scattered/diffused light received across the skin site.

In the context of the present principles described herein, the terms 'scattering' and 'diffusion' is a reference to the deviation of light rays from their straight trajectory.

In the context of the present principles described herein, the term 'dispersion', and variations thereof, is a reference to the general distribution or spread of light (rays).

In one embodiment, the meeting or contacting of the portion of light emitted from the light emitting means with the reflecting portion of the reflector means or module is configured operable so as to substantially reduce acute or direct incidence of light received by the skin site and or substantially acute or direct reflection of light from the skin site.

In one embodiment, the meeting or contacting of the portion of light emitted from the light emitting means with the reflecting portion of the reflector means or module is configured operable so as to facilitate scattering or dispersing/diffusing of the received light for projection on to the skin site for facilitating a substantially uniform or even distribution of light to be receivable across the skin site.

In one embodiment, the reflecting portion of the reflector means or module is configured so as to disperse/diffuse or scatter light received from the light emitting means or module. In this manner, light dispersed/diffused or scattered by way of the meeting/contacting with the reflecting portion of the reflector means or module is receivable at the skin site at generally obtuse angles of incidence therewith.

Consistent with the principles described herein, embodiments of the illumination arrangement seek to reduce substantive or extreme differences in light intensities that are reflected from the skin site toward any imaging means by which an examination of the skin site is to be undertaken. In some embodiments, such a reduction in the substantive or extreme differences in light intensities of the reflected light (from the skin site) may operate to lessen of reduce the requirements for image correction. For example, decrease(s) in directly or acutely reflected light back to an image capturing means/module (indicative of conventional illumination arrangements used in existing skin examination devices) has been found to create a corresponding increase of visibility of subsurface cell structures of the skin site under examination.

In one embodiment, another portion of light emitted from the light emitting means or module and receivable by the skin site without meeting or contacting the reflecting portion of the reflector means or module.

In one form, the reflector means or module comprises a body having a profile reminiscent or substantially that of a flat or planar annular disk.

In one embodiment, the reflecting portion is carried by one side of the body of the reflector means or module, which side is arrangeable so as to substantially face and align parallel with the skin site.

In one embodiment, the body of the reflector means or module is orientable so as to align the side of the body carrying the reflecting portion so that it aligns substantially perpendicular with an axis (for example, an optical axis) of the illumination arrangement relative to which light is radiated toward, and reflected from, the skin site.

In another embodiment, a portion of the reflecting portion comprises or is configured with any of the following: a metallic material, a reflective surface, a reflective mirror or reflective mesh (e.g., a metallic material or substrate), a surface profile of generally uneven or non-uniform form, a surface profile comprising a pattern (regular or otherwise) of embossments or protuberances or raised formations, a metallic material comprising a regular mesh of raised formations (e.g., ridges or hatchings), ridge like formations, a coating providing a texture comprising any of the aforementioned features.

In another embodiment, the light emitting means or module comprises a plurality of light emitting elements positioned on at or near a perimeter of the body of the reflector means or module.

In a further embodiment, the plurality of light emitting elements are arranged equidistant with respect to each other.

In one embodiment, one or more of the plurality of light emitting elements are arranged so as to emit or radiate a first portion of light toward the reflecting portion carried by the body of the reflector means or module.

In one embodiment, one or more of the plurality of light emitting elements are arranged so as to emit or radiate a second portion of light for projection on to the skin site or away from the reflector means or module.

In a further embodiment, one or more of the plurality of light emitting elements are configured having a scope of light emission or dispersion of about 120 degrees, which scope lies on a plane aligned substantially perpendicular relative to the reflecting portion of the reflector means or module so that at least a portion of the emitted light meets or makes contact with the reflecting portion so as to be dispersed/diffused/scattered.

In a further embodiment, the body of the reflector means or module comprises an aperture arranged substantially concentric with the body's perimeter through which light reflected from the skin site passes to any of: an imaging means or module, a distortion correction lens, a lens of the liquid lens type, and or having passed through any of: a distortion correction lens, a polarising filter. In one form, the aperture is substantially concentric with the axis of the illumination arrangement.

In one embodiment, any of the plurality of light emitting elements are configured so that one or more characteristics of the light emitted from the relevant of the light emitting element(s) are adjustable or controllable. For example, characteristics of the light emitted from the light emitting element may comprise, for example, a light intensity, a colour. The skilled reader will appreciate other characteristics that can be configured adjustable or controllable.

In one embodiment, the plurality of light emitting elements are comprised of first and second sets of light emitting elements, each of the first and second sets of light emitting elements configured controllable by way of respective controller modules, wherein any of the plurality of light emitting elements are configured operable so that one or more characteristics of the light emitted from the relevant of the light emitting element(s) are adjustable or controllable.

In another embodiment, the light emitting elements of the first and second sets of light emitting elements are arranged in an interleaving or alternating manner at or near a perimeter of the body of the reflector means or module. For example, a light emitting element of one of the sets of light emitting elements is positioned adjacent or intermediate/between light emitting element(s) of the alternate set of light emitting elements.

In one form, operation of either of the first and second sets of light emitting elements corresponds to a respective mode of operation of the illumination arrangement. For example, operation of the first set of light emitting elements corresponds to a mode of operation configured operable for enabling a first examination method to be undertaken with the device (e.g., an examination of a generally dry skin site), and operation of the second set of light emitting elements corresponds to another mode of operation configured operable for enabling a second examination method to be undertaken with the device (e.g., an examination of a skin site to which an appropriate fluid or oil has been applied).

In a further embodiment, one or more portions of an internal surface of a housing in which the illumination arrangement operates is configured for reflecting scattered or diffused/dispersed light received from the reflector means or module for projection on to the skin site.

In one embodiment, the body of the reflector means or module is provided in the form of a printed circuit board, and or to which any of the light emitting elements is/are attached or in electrical connection with appropriate circuitry provided hosted by the circuit board for operation.

The illumination arrangement may further comprise or be arranged operable with a first polariser (e.g., a polarising filter) arranged in the radiated light path between the illumination means or module and the skin site.

The illumination arrangement may further comprise or be arranged operable with a second polariser (e.g., a polarising filter) arranged in the reflected light path between the skin site and the imaging means or module. In one operable use with the second polariser, when the light source is of a single or uniform angle engaging or entering the skin site, less dispersion (light distribution or spread) occurs sub-surface after entering the skin. As such, the second polariser will tend to filter out most of the light reflected from the skin site. With the reflected scattered or diffused light received by the skin, there is more dispersion (light distribution or spread) after entering the skin and therefore the sub-surface structure becomes brighter as a larger scope of light reflected from the skin site avoids the effect of the second polariser.

In one embodiment, the second polariser polarises light in an orientation substantially perpendicular to an orientation that the first polariser polarises light.

In another embodiment, the first polariser is configured so as to enable portions of light to be respectively polarised and unpolarised for projection on to the skin site.

According to a second aspect, there is provided an optical arrangement for use with a device operable for use in the examination of a skin site, the device having or arranged operable with an illumination means or module operable for illuminating the skin site and an imaging means or module operable with a lens by way of which light is received by the imaging means or module, the optical arrangement comprising:

a further lens configured operable for modifying a light path received thereby, wherein the optical arrangement is configured operable so that on illumination by way of the illumination means or module light is reflected from the skin site toward the imaging means or module in a reflected light path, wherein the further lens is arranged in the reflected light path between the skin site and the lens of the imaging means or module, and configured so as to be operable or co-operable with the lens of the imaging means or module so that the reflected light path is subject to a modification operating to substantially correct for one or more optical distortion effects prior to reaching the imaging means or module.

In one embodiment, the lens of the imaging means or module is one of the 'liquid lens' type. In the context of the principles described herein, the term 'liquid lens' is a reference to a lens formed using the natural shape of liquid droplets. In this manner, liquid lenses have been found to have similar properties to aspherical lens types which exhibits a flatter field of focus. Advantageously, this can allow a single lens element to replace complex lens design for small microscopy cameras (such as, for example, pin-hole cameras).

In one embodiment, the further lens comprises a distortion correction lens that is configured for modifying the reflected light path as appropriate so as to enable the imaging means or module to receive or capture an image that is substantially, to the extent possible, absent of one or more distortion effects.

In embodiments of the present optical arrangement where a liquid lens has been employed, it has been found that by shifting the liquid lens' focal distance away from, for example, a camera sensor, the optical result achieved can be close to the quality of microscopy. However, such an arrangement can suffer from optical effects such 'fish-eye' effect or very heavy 'barrel' distortion. The presence of barrel distortion can result in misdiagnosis in dermoscopy because the shape of, for example, a mole or skin condition, can become distorted. The developers of the presently described technology have discovered advantage in that by placing a second aspherical achromatic lens configured for distortion correction in front of the liquid lens, it is possible to induce a 'pin-cushion' effect which can operate to reduce or cancel out the fish-eye/barrel distortion of the liquid lens. In some arrangements, the liquid lens is required to be unfocused to compensate the additional focal length of the distortion correction lens. The final result can be a very low distortion skin imaging system suitable for the field of dermascopy.

The optical arrangement may further comprise a first polariser (e.g., a polarising filter) arranged in the radiated light path between the illumination means or module and the skin site.

The optical arrangement may further comprise a second polariser (e.g., a polarising filter) arranged in the reflected light path between the skin site and the imaging means or module.

The second polariser may be arranged in the reflected light path between the distortion correction lens and the imaging means or module.

In one embodiment, the second polariser polarises light in an orientation substantially perpendicular to an orientation that the first polariser polarises light.

In another embodiment, the first polariser is configured so as to enable portions of light to be respectively polarised and unpolarised for projection on to the skin site.

In one embodiment, the imaging means or module is configured operable for capturing an image. In such an embodiment, the imaging means or module may be provided in the form of an image capturing means or module (e.g., a digital camera).

Embodiments of the illumination means or module may comprise embodiments of the illumination arrangement according to the first aspect, or as otherwise described herein.

According to a third aspect, there is provided an optical arrangement for use with a device operable for use in the examination of a skin site, the device having or arranged operable with an illumination means or module operable for illuminating the skin site and an imaging means or module, the optical arrangement comprising:

a lens of the liquid lens type arranged in operable association with the imaging means or module, and a distortion correction lens, wherein the optical arrangement is configured operable so that on illumination by way of the illumination means or module light is reflected from the skin site toward the imaging means or module in a reflected light path, and wherein the distortion correction lens is arranged in the reflected light path between the skin site and the liquid lens.

Embodiments of the optical arrangement of the present aspect may comprise any of the features, either individually or in combination, described in relation to the optical arrangement of the second aspect, or as otherwise described herein.

In accordance with a fourth aspect, there is provided a device for examination of a skin site comprising:

a housing with a central or optical axis alignable substantially perpendicular to the skin site;

an illumination means or module arranged within the housing;

an imaging means or module arranged within the housing;

a power supply means or module;

wherein the housing incorporates or provides a substantially planar plate of transparent plastic or glass material which contacts the skin site, wherein light is radiated from the illumination means or module to the skin site in a radiated light path, and wherein light is reflected from the skin site to the imaging means or module in a reflected light path.

Embodiments of the above-described aspects, and those described below, may comprise, either individually or in combination, any of the following described features.

The illumination means or module is configured or arranged operable for emitting and dispersing or scattering light (hereinafter, light emitting and dispersing means or module).

In one embodiment, the housing is configured so as to incorporate or provide a substantially planar plate member which, in operation of the device, is brought into contact with the skin site for aligning the central or optical axis so as to be substantially normal or perpendicular to the skin site. The plate may be generally formed from a suitable transparent material, for example, plastic or glass, and operates to assist in substantially flattening (to the extent possible) the skin site thereby allowing for reproducible image receiving/capturing. The plate may stretch or smooth out the skin site for inspection/examination. For the reasons of hygiene and cleaning, glass, and in particular a scratch-proof, tough, hardened mineral glass, may offer advantage for use as the material for the plate. The plate also seeks to prevent foreign bodies from entering the device.

In one embodiment, the imaging means or module is configured operable for receiving and or capturing an image. In such an embodiment, the imaging means or module may comprises or be provided in the form of an image capturing means of module (e.g., a digital camera).

In another embodiment, the device further comprises a distortion correction lens arranged in the reflected light path between the skin site and the imaging means or module.

In one embodiment, the device further comprises a first polariser (e.g., a polarising filter) arranged in the radiated light path between the light emitting and dispersing means or module and the skin site.

In a further embodiment, the device further comprises a second polariser (e.g., a polarising filter) arranged in the reflected light path between the skin site and the imaging means or module. In one form, the second polariser may be arranged in the reflected light path between the distortion correction lens and the imaging means or module.

In one embodiment, the first polariser and the second polariser are arranged or configured operable so as to provide the device with a cross polarisation filter arrangement for use in reducing unwanted specular reflections.

In another embodiment, the second polariser polarises light in an orientation substantially perpendicular to an orientation that the first polariser polarises light.

In one embodiment, the radiated light path and the reflected light path travel or operate relative or with respect to the central or optical axis.

In a further embodiment, the first polariser is configured with one or more apertures for enabling a portion of light of the radiated light path to pass therethrough.

In another embodiment, the light emitting and dispersing means or module, the imaging means or module, and or the first and or second polarisers, are arranged so as to be substantially concentric with the central or optical axis.

In a further embodiment, the light emitting and dispersing means or module comprises a body having a profile reminiscent of a flat or planar annular disk oriented substantially perpendicular to the axis of the device.

In one embodiment, the light emitting and dispersing means or module comprises a profile or form substantially that of a substantially planar or flat annular disk.

In one arrangement, the light emitting and dispersing means is a substantially flat annular disk that, for operable use, is oriented so as to align substantially perpendicular with or to the central or optical axis of the device.

In a further embodiment, the light emitting and dispersing means or module is provided or exemplified in the form of a printed circuit board.

In one embodiment, the light emitting and dispersing means or module may be provided or exemplified in the form of a printed circuit broad having a profile of a substantially flat annular disk that, for operable use, is oriented substantially perpendicular to the central or optical axis of the device.

In another embodiment, a surface of a portion of the light emitting and dispersing means or module is reflective.

In one embodiment, the light emitting and dispersing means or module is orientated so that, for operable use of the device, the reflective surface portion faces the skin site.

The light emitting and dispersing means or module may incorporate a plurality of light emitting elements.

In a further embodiment, the light emitting and dispersing means or module has a plurality of light emitting elements arranged on at or near a perimeter or circumference of the planar or flat annular disk. In this manner, the light emitting and dispersing means or module has a plurality of light emitting elements arranged on at or near the perimeter of the body of the illumination means or module.

In one form, the light emitting elements may be arranged equidistant to each other.

In one embodiment, the light emitting elements are arranged so as to provide a substantially uniform or even distribution of emitted light about the light emitting and dispersing means or module.

In another embodiment, any of the light emitting elements are provided in the form of light emitting diodes.

In one arrangement, any of the light emitting elements may be provided in the form of light emitting diodes connected to circuitry of the printed circuit board of the light emitting and dispersing means or module.

In a further embodiment, the light emitting elements are oriented so as to emit light on to the reflective surface portion of the light emitting and dispersing means or module.

In a further embodiment, any of the light emitting elements are configured having about a 120° dispersion angle on or relative a plane aligned substantially perpendicular to the reflective surface.

In another embodiment, the reflected light path traverses the central or optical axis and passes through a centre of the light emitting and dispersing means or module.

In one embodiment, the reflective surface portion of the light emitting and dispersing means or module is configured so as to be substantially uneven or of a non-uniform nature so as to disperse/diffused or scatter light received from the light emitting elements of the light emitting and dispersing means or module away from the reflective surface portion.

In one embodiment, the reflective surface portion of the light emitting and dispersing means or module is configured having a generally regular pattern of embossments, protuberances or raised portions which renders the general form of the reflective surface portion in a substantially uneven or non-uniform manner. It will be appreciated that the uneven nature of the reflective surface portion could be achieved in a number of ways, including, for example, an appropriate substrate exemplifying an appropriate patterned texture or hatchings configured operable for reflecting light received thereby in a manner that serves to disperse/diffused or scatter such light away from the reflective surface portion.

In a further embodiment, the reflective surface portion of the light emitting and dispersing means or module has a substantially regular pattern of ridges.

In one embodiment, the reflective surface portion is rendered reflective with a mesh-like uneven coating. The mesh-like coating may form a regular pattern.

In a further embodiment, one or more portions of an inner surface of the housing adjacent the planar plate are configured so as to be reflective. In this manner, light received from the light emitting and dispersing means or module is reflectable for projection on to the skin site.

In another embodiment, the imaging means is provided in the form of a digital camera.

In a further embodiment, the power supply means or module is configured for supplying or distributing electrical power to any of the on-board components of the device requiring electrical power for operation.

In one embodiment, the power supply means or module is configured for receiving electrical energy or power from a source of electrical energy or power (e.g., mains power source, battery power source, and which may be external of the device or internal/on-board the device) for supplying or distributing electrical energy or power to any of the on-board components of the device requiring electrical power for operation.

In one embodiment, the power supply means or module is provided internal or on-board the device. The power supply means or module may be configured operable for receiving electrical energy or power from an external source of electrical energy or power for supply/distribution to or any of the on-board components of the device through a cord (for example, via a USB or like cable).

In another embodiment, the power supply means or module may be internal to the device. In one form, the power supply means or module comprises a battery provided internal or on-board the device.

In an embodiment, the device further comprises or incorporates a control means or module.

In another embodiment, the control means or module is adapted so as to signal the imaging means or module to capture an image. In this manner, the device may comprise or incorporate a control means or module, such as for example, a button or touchpad, that when activated, signals the device to operate for capturing an image.

In a further embodiment, the device is arranged or configured so as to be operably associable or connectable with an external electronic device, such as for example, a non-portable or portable computer, a desktop computer, a laptop, a portable or mobile device, table or like electronic device, for communicating with the electronic device for undertaking operational events (e.g., triggered by a user or operator of the relevant electronic device), such as for example, data transfer, image capture.

In another form, the device may be signalled to capture an image (or otherwise operate) remotely from an external electronic device, computer system or computer network (via, for example, a wired or wireless communication arrangement).

The device may be connected to or associated with an external computer via a cable or wireless connection. The external computer may provide power to the device as an external power supply means or module.

The device may be arranged or configured operable with appropriate hardware or circuitry so as to be capable of interfacing via wireless or wired communication with a computing network or cloud-based network/system, comprising, for example, a non-portable or portable computer, a desktop computer, a laptop, a portable or mobile device, table or like electronic device.

In one form, the device is configured operable so that the light emitting elements may activate upon the device receiving power.

In another form, the device is configured so that the activation of the light emitting elements may be controlled or controllable by way of an appropriately configured control system.

The light emitting elements may be controlled or controllable modally to allow for adjustable light levels, sequenced activation and other similar requirements within the scope of understanding of a person skilled in the art.

In some embodiments, the emitting and dispersing means or module may comprise any embodiment arranged or configured in accordance with:

(i) the illumination arrangement of the first aspect described above or as otherwise described herein, and or, (ii) the optical arrangement(s) of the second or third aspects described above or as otherwise described herein.

Embodiments, of the illumination arrangement, optical arrangement, and the devices of the aspects described herein may be configured so as to accommodate or operate with an oil immersion method as previously described.

In an embodiment, the housing is configured so as to be substantially dustproof. In one embodiment, the housing is configured so as to be substantially splashproof. The housing may be configured so as to be substantially waterproof or water resistance.

In another embodiment, the device further comprises a handle affixed to or incorporated with the housing. In one form, the handle may be removably attachable with the housing.

According to a fifth aspect, there is provided a device for use in an examination of a skin site comprising:

a housing, an illumination means or module arranged within the housing, an imaging means or module arranged within the housing, a lens of the liquid lens type arranged in operable association with the imaging means or module, and a distortion correction lens, wherein, in use, the device is configured operable so that:

(i) light is radiated by way of the illumination means or module for projection on to the skin site in a radiated light path; and (ii) light is reflected from the skin site toward the imaging means or module in a reflected light path;

wherein the distortion correction lens is arranged in the reflected light path between the skin site and the liquid lens.

Embodiments of the device of the fifth aspect may comprise any of the features (either individually or in combination) described in relation to the device of the fourth aspect or as otherwise described herein.

Furthermore, embodiments of the device(s) of the fourth and or fifth aspects may comprise any of the features (either individually or in combination) described in relation to the illumination arrangement of the first aspect (or as otherwise described herein) and or the optical arrangement(s) of the second or third aspects (or as otherwise described herein).

In accordance with another aspect, there is provided a device for examination of a skin site comprising:

a housing with a central axis perpendicular to the skin site;

a light emitting and dispersing means arranged within the housing;

an imaging capturing means arranged within the housing;

a power supply;

wherein the housing incorporates a substantially planar plate of transparent plastic or glass material which in use contacts the skin site, wherein light is radiated from the light emitting and dispersing means to the skin site in a radiated light path, and wherein light is reflected from the skin site to the imaging capturing means in a reflected light path.

In accordance with a further aspect, there is provided a method of examining skin using a device arranged substantially in accordance with the fourth or fifth aspects, or an embodiment of a device as otherwise described herein, whereby the method comprises the steps of:

selecting a skin site, positioning the device such that the substantially planar plate contacts the skin site, activating the device so as to emit light within the device whereby a significant amount of light is scattered, dispersed or diffused within the device, and projecting the light on to the skin site;

whereby light reflected from the skin site travels the reflected light path to the image receiving or capturing means or module which receives/captures image data.

In one embodiment, light is polarised by a first polariser prior to being projected on to the skin site.

In another embodiment, light in the reflected light path passes through a distortion correction lens prior to reaching the image receiving or capturing means or module.

In a preferred embodiment, light in the reflected light path is polarised by a second polariser prior to reaching the image receiving or capturing means or module.

In a further embodiment, the image receiving or capturing means or module transmits the image data to an external electronic device (such as for example, a computer). Any such transmission may be via a wired or wireless connection between the device and the external electronic device.

In another embodiment, the image data is modified or modifiable using software.

According to a further aspect, there is provided a method for illuminating a skin site in the examination of the skin site, the method comprising:

configuring a reflector means or module so as to have a reflecting portion configured operable for reflecting light received thereby, configuring a light emitting means or module so as to be operable between the reflector means or module and the skin site, configuring the light emitting means with the reflector means or module so that a portion of light emitted from the light emitting means or module meets or makes contact with the reflecting portion, and configuring the reflector portion of the reflector means or module so that the meeting or contact between the portion of light emitted from the light emitting means or module and the reflecting portion is operable so as to promote scattering or diffusion of light reflected from the reflecting portion for projection on to the skin site for increasing the variability or non-uniformity of incidence of the reflected scattered/diffused light received across the skin site.

According to another aspect, there is provided an imaging method for a device operable for use in the examination of a skin site, the device having or arranged operable with:

an illumination means or module arranged operable for illuminating the skin site, and an imaging means or module operably associated with a lens by way of which light is received by the imaging means or module, the illumination means or module operable for illuminating the skin site so that light is reflected therefrom toward the imaging means or module in a reflected light path, the imaging method comprising:

configuring a further lens so as to be operable for modifying a light path received thereby so as to be operable or co-operable with the lens of the imaging means or module so that the reflected light path is subject to a modification operating to substantially correct for one or more optical distortion effects prior to reaching the imaging means or module, arranging the further lens so as to be in the reflected light path between the skin site and the lens of the imaging means or module, and, causing the skin site to be illuminated by way of the illumination means or module so that light is reflected from the skin site toward the imaging means or module in the reflected light path.

In accordance with another aspect, there is provided a device for examination of a skin site comprising any embodiment of an illumination means or module as described herein, arranged operable with any embodiment of an optical arrangement as described herein.

In accordance with a further aspect, there is provided a method of using any embodiment of a device as described herein.

In accordance with another aspect, there is provided a method of examining a portion or region of skin using any embodiment of a device as described herein.

It will be understood by the reader that any document, reference, patent application or patent cited in this text is expressly incorporated herein in their entirety by reference, which means that it should be read and considered by the reader as part of this text.

That the document, reference, patent application, or patent cited in this text is not repeated herein is merely for reasons of conciseness.

In this specification, where a literary work, act or item of knowledge (or combinations thereof), is discussed, such reference is not an acknowledgment or admission that any of the information referred to formed part of the common general knowledge as at the priority date of this application. Such information is included only for the purposes of providing context for facilitating an understanding of the inventive concept/principles and the various forms or embodiments in which those inventive concept/principles may be exemplified.

Various aspects, examples or embodiments described herein can be practiced alone or in combination with any one or more of the other described aspects, examples or embodiments, as will be readily appreciated by those skilled in the relevant art. The various described aspects, examples or embodiments can optionally be provided in combination with one or more of the optional features described in relation to the other aspects, examples or embodiments. Furthermore, optional features described in relation to one aspect, example or embodiment can optionally be combined alone or together with other features described in relation different aspects, examples or embodiments.

For the purposes of summarising the various aspects, examples, or embodiments exemplifying the principles described herein, certain aspects, advantages and novel features have been described above and herein. It is to be understood, however, that not necessarily all such advantage(s) may be achieved in accordance with any particular embodiment or carried out in a manner that achieves or optimises one advantage or group of advantages as taught herein without necessarily achieving other advantage(s) as may be taught or suggested herein.

BRIEF DESCRIPTION OF DRAWINGS

Further features of the inventive principles are more fully described in the following description of one or more non-limiting examples or embodiments thereof. This description is included solely for the purposes of exemplifying the inventive principles. It should not be understood as a restriction on the broad summary, disclosure or description as set out above or herein.

The inventive principles underlying the present invention will now be described, by way of example, with reference to the accompanying drawings, in which.

Figure 1:
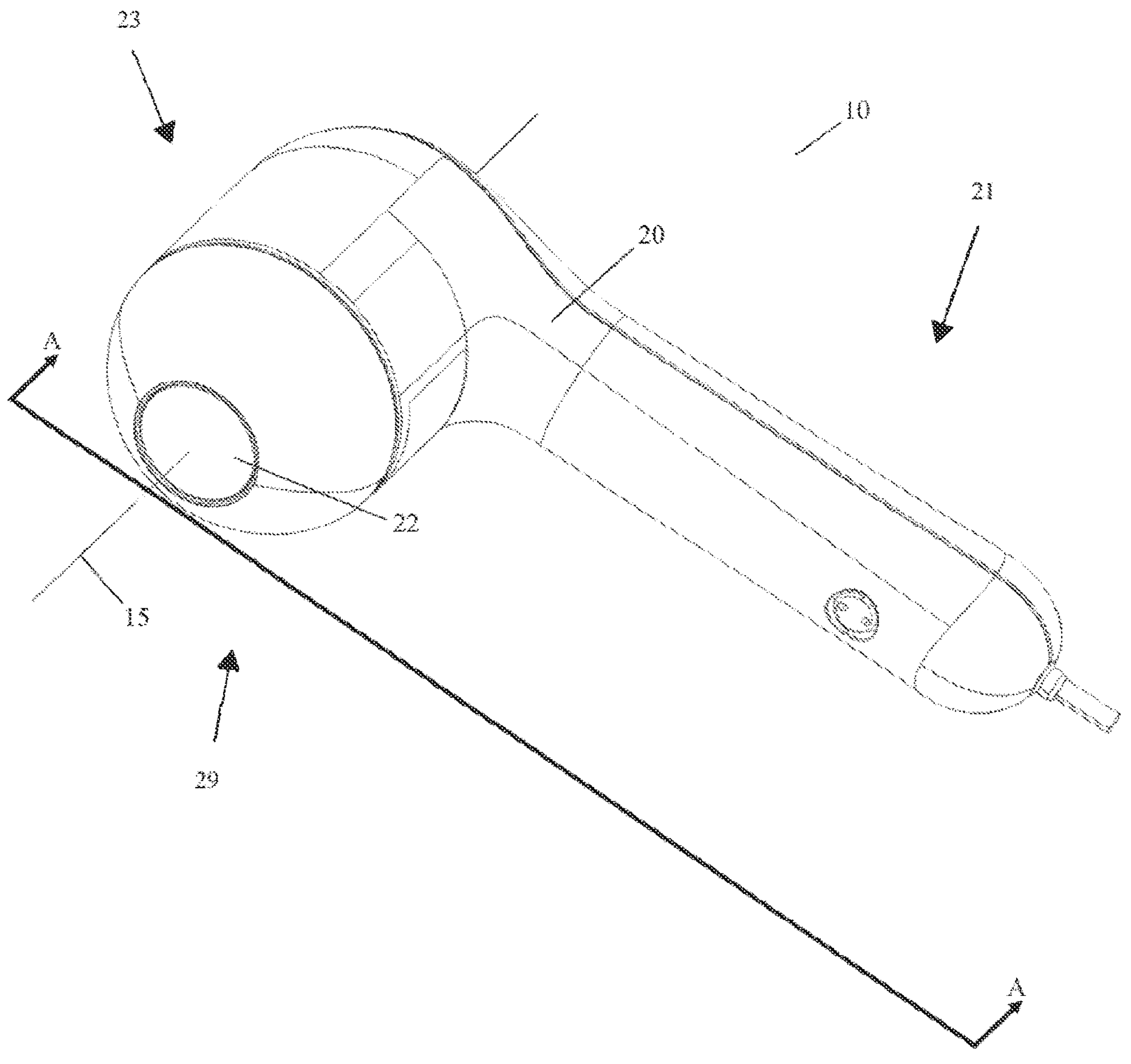
FIG. 1 is a perspective view of a device for examination of a skin site in accordance with an embodiment of the present invention.

In the figures, like elements are referred to by like numerals throughout the views provided. The skilled reader will appreciate that elements in the figures are illustrated for simplicity and clarity and have not necessarily been drawn to scale. For example, the dimensions and/or relative positioning of some of the elements in the figures may be exaggerated relative to other elements to facilitate an understanding of the various embodiments exemplifying the principles described herein. Also, common but well understood elements that are useful or necessary in a commercially feasible embodiment are often not depicted in order to provide a less obstructed view of these various embodiments. It will also be understood that the terms and expressions used herein adopt the ordinary meaning as is accorded to such terms and expressions with respect to their corresponding respective areas of inquiry and study except where specific meanings have otherwise been set forth herein.

It should be noted that the figures are schematic only and the location and disposition of the components can vary according to the particular arrangements of the embodiment(s) as well as of the particular applications of such embodiment(s).

Specifically, reference to positional descriptions, such as 'lower' and 'upper', and associated forms such as 'uppermost' and 'lowermost', are to be taken in context of the embodiments shown in the figures, and are not to be taken as limiting the scope of the principles described herein to the literal interpretation of the term, but rather as would be understood by the skilled reader.

Embodiments described herein may include one or more range of values (e.g., size, displacement and field strength etc). A range of values will be understood to include all values within the range, including the values defining the range, and values adjacent to the range which lead to the same or substantially the same outcome as the values immediately adjacent to that value which defines the boundary to the range.

Other definitions for selected terms used herein may be found within the detailed description and apply throughout. Unless otherwise defined, all other scientific and technical terms used herein have the same meaning as commonly understood to one of ordinary skill in the art to which the embodiment(s) relate.

DETAILED DESCRIPTION

The words used in the specification are words of description rather than limitation, and it is to be understood that various changes may be made without departing from the spirit and scope of any aspect of the principles described herein. Those skilled in the art will readily appreciate that a wide variety of modifications, variations, alterations, and combinations can be made with respect to the above-described embodiments without departing from the spirit and scope of any aspect of the principles described, and that such modifications, alterations, and combinations are to be viewed as falling within the ambit of the inventive concept.

Throughout the specification and the claims that follow, unless the context requires otherwise, the word "comprise" or variations such as "comprises" or "comprising", will be understood to imply the inclusion of a stated integer or group of integers but not the exclusion of any other integer or group of integers.

Furthermore, throughout the specification and the claims that follow, unless the context requires otherwise, the word "include" or variations such as "includes" or "including", will be understood to imply the inclusion of a stated integer or group of integers but not the exclusion of any other integer or group of integers.

Figure 3:
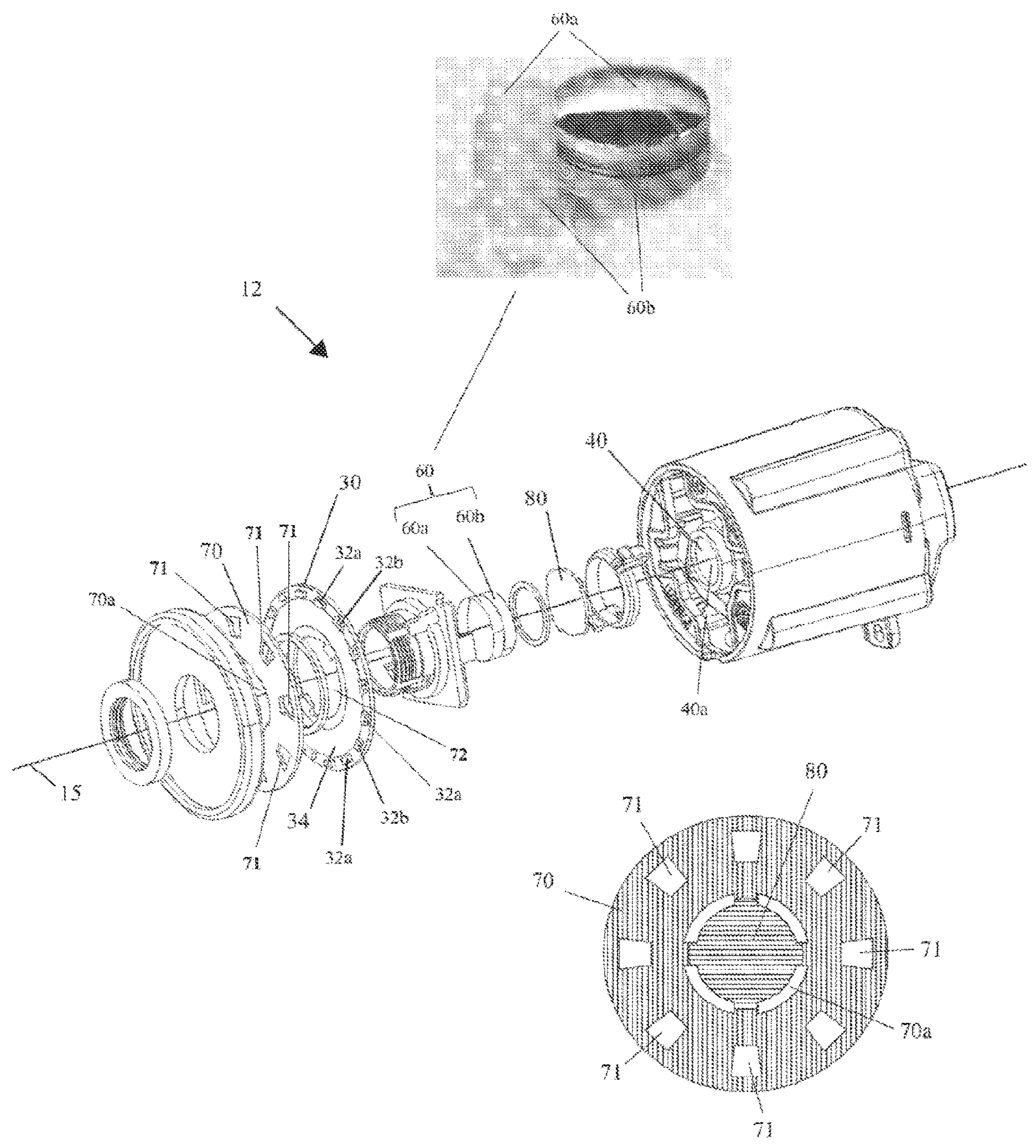
FIG. 3 is an exploded view of a component module of the device depicted in FIG. 1: the upper inset image of FIG. 3 shows one embodiment of the distortion correction lens (60) used in the device (10), and the lower inset image of FIG. 3 shows the alignment of the first (70) and second (80) polarisers when looking along the axis (15) toward the digital camera (40).
Figure 4:
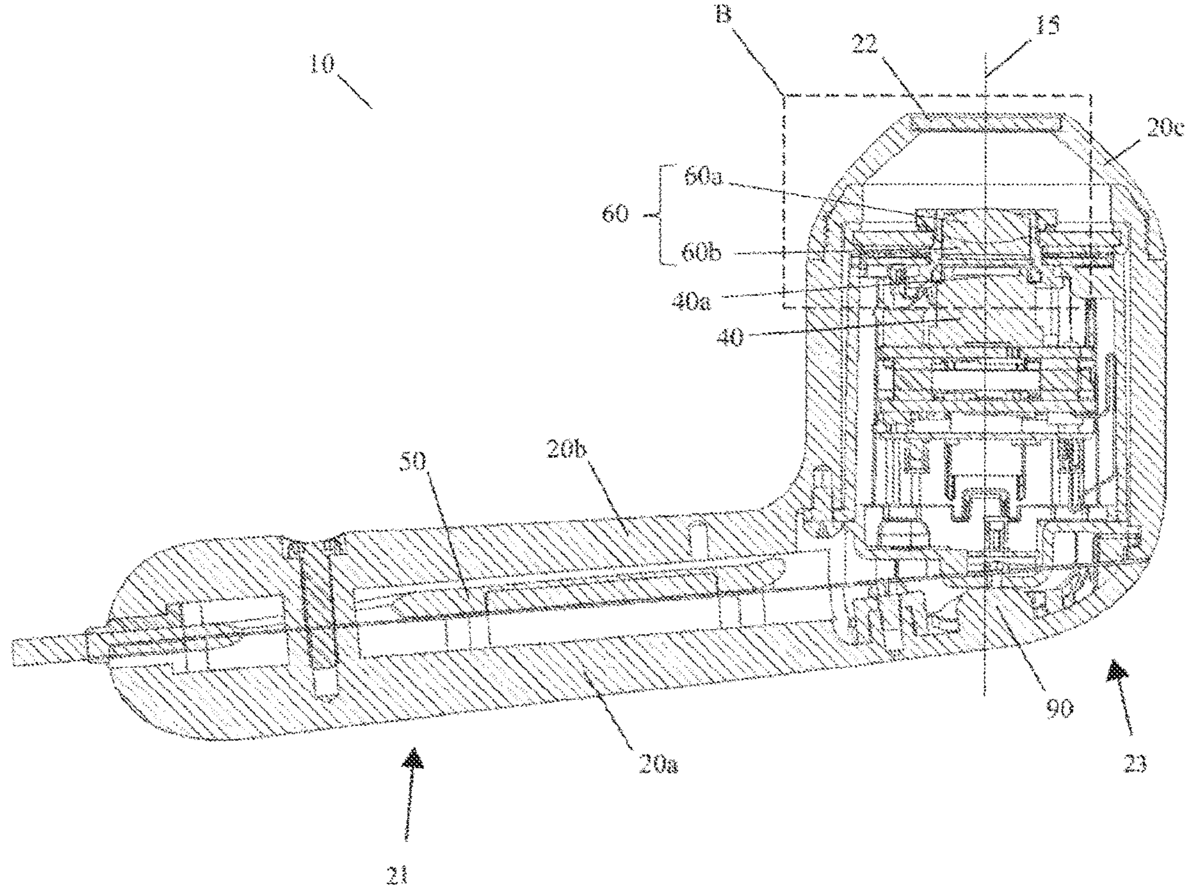
FIG. 4 is a cross-sectional view A-A of the device depicted in FIG. 1.
Figure 5:
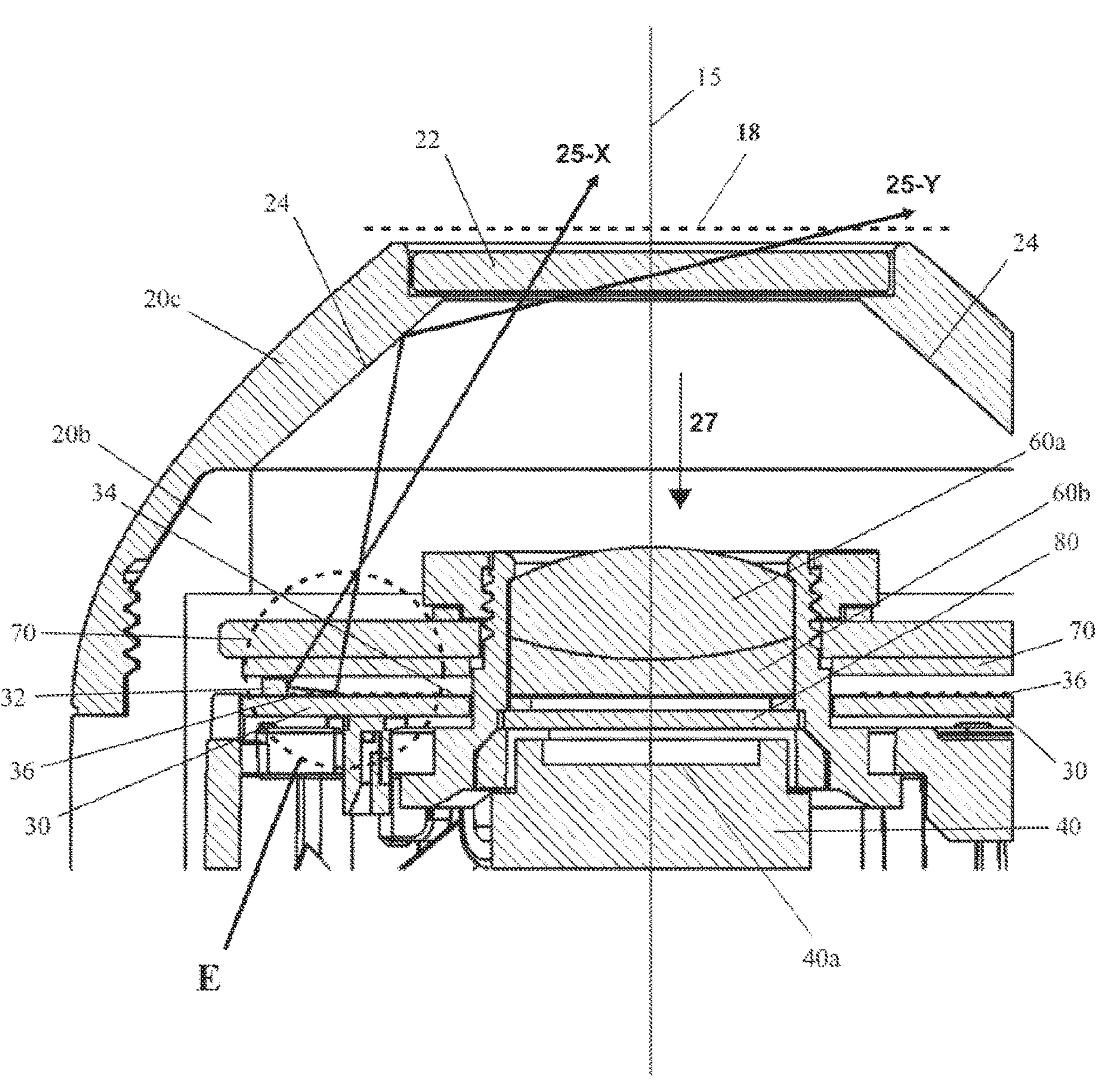
FIG. 5 shows a cross-section view of a region identified by reference "B" in FIG. 4.

FIGS. 1 to 5, 12, and 13, show one embodiment of a device 10 exemplifying the principles described herein that are particularly adapted for handheld use for use in the examination of a target skin site (hereinafter, skin site 18—shown in FIG. 5 for reference purposes).

As will be described below, aspects of the device 10 include an illumination arrangement that operates to illuminate the skin site 18 in a manner that seeks to reduce substantive (or, to the extent possible, extreme) differences in light intensities that are reflected from the skin site toward any imaging means by which an examination of the skin site is to be undertaken. Broadly, the illumination arrangement seeks to promote scattered or diffused light being received by the skin site 18 for promoting increased distribution of the received light sub-surface of the skin site thereby increasing the scope of light reflected from the skin-site for imaging/diagnostic purposes.

The device 10 also employs an optical arrangement which operably seeks to achieve an improved optical image for use in the field of dermascopy that is of low distortion and/or close to the quality of that achieved in the field of microscopy.

With reference to FIGS. 1 to 5, the device 10 comprises a housing 20, a portion of which, at least in part, defines a generally central axis 15 (hereinafter, central axis 15), and an illumination means or module operable for emitting and dispersing/scattering light (hereinafter, light emitting and dispersing module 30) and arranged within the housing 20. The device 10 further comprises an imaging module for receiving/capturing the image of the skin site 18. In the form of the device 10 described herein, the imaging module is provided in the form of a digital camera 40 that is arranged within the housing 20. The digital camera 40 has or is arranged operably with an associated lens **40*a* by way of which light reflected from the skin site 18 is received by the digital camera 40 (or whatever imaging module might be employed). The central axis 15 may also be referred to as an optical axis in that light radiated from the light emitting and dispersing module 30, and reflected from the skin site 18 to the digital camera 40, travels relative (or with respect) to the central/optical axis 15, as is shown in FIG. 5**.

The imaging module may comprise any module that is suitably operable for receiving light corresponding to an image of the skin site 18. The imaging module may be configured operable for enabling an image of the skin site 18 to be captured for, for example, downstream processing (e.g., using an external electronic device hosting appropriate software) or local/external storage. Furthermore, the imaging module may be configured operable for enabling an image of the skin site 18 to be inspected in real-time for manual inspection/examination of the skin site 18 by an examining clinician.

The housing 20 is configured so as to incorporate or provide a substantially planar plate member (hereinafter, plate 22) which, in operation of the device 10, is brought into contact with the skin site 18 for aligning the central axis 15 so as to align substantially normal or perpendicular to/with the skin site 18. The plate 22 is generally formed from a suitable transparent material, for example, plastic or glass, and operates to assist in substantially flattening (to the extent possible) the skin site 18 thus allowing for reproducible image receiving/capturing which can be compared against one another. The plate 22 may stretch or smooth out the skin site 18 for inspection/examination purposes. For the reasons of hygiene and cleaning, glass, and in particular a scratch-proof, tough, hardened mineral glass, is preferred for use as the material for the plate 22. The plate 22 also seeks to prevent foreign bodies from entering the device 10.

In some arrangements of the device 10, there may be a wall, border or skirt structure provided or formed around the substantially planar plate 22 that seeks to prevent external light from entering the area of the skin site 18 and prospectively distorting the results of the examination.

The device 10 is configured operable so that in use light is radiated from the light emitting and dispersing module 30 to the skin site 18 in a radiated light path 25; and light is reflected from the skin site 18 to the digital camera 40 in a reflected light path 27.

Traditional devices that project, emit, or radiate light directly on to a skin site have to adjust to accommodate or counteract the significant proportion of the light which is reflected back to the relevant imaging means employed.

In one aspect, and consistent with the principles described herein, the device 10 is configured so that the illumination arrangement employed specifically diffuses or scatters the light (diffused/scattered light being indicated by reference 25-Y in FIG. 5) prior to projection on to the skin site 18, thus reducing occurrences of localised light intensities due to directly or acutely reflected light in the reflected light path 27 thereby allowing the digital camera 40 to capture an image without extreme differences in light intensities and/or lessening the requirements for image correction. The decrease in directly reflected light back to an image receiving/capturing means/module (indicative of conventional illumination arrangements used in existing skin examination devices) creates a corresponding increase of visibility of subsurface cell structures of the skin site 18.

Accordingly, for imagery capture at such short distances using a device that shines the full intensity of light directly at a skin site commonly results in local hot-spots and uneven illumination intensity which is detrimental to the quality of the final image. An aspect of the present invention seeks to address this detriment by utilising a diffused, scattered or dispersed light which has been diffused and/or scattered by the light emitting and dispersing module 30. For example, as can be seen with reference to FIG. 5, the diffused/scattered light 25-Y engages or enters the skin of the skin site 18 at generally obtuse incidence angles decreasing the frequency of direct reflection from the skin surface (to the relevant image capturing module), thereby evenly illuminating the skin of the skin site 18 and allowing sub-surface cell structures to be perceived more clearly—and from a relatively close distance from the skin site 18. In this manner, direct reflection of light from the skin surface back towards the relevant image capturing module (for example, digital camera 40) can be reduced.

It has been determined that it is not necessary that 100% of the light emitted by suitable light emitters be diffused in this manner, as some direct light is not undesirable. In some cases, some direct light (directly radiated light from the light emitters (32) being indicated by reference 25-X in FIG. 5) may allow for, in some circumstances, a brighter and clearer image.

The device 10 further employs an optical arrangement which comprises a distortion correction lens 60 which is arranged in the reflected light path 27 between the skin site 18 and the imaging module (i.e. digital camera 40). In one form, and with reference to FIGS. 3, 4, and 5, the distortion correction lens 60 is comprised of two optical lenses 60*a*, 60*b* fused together having respective densities different from one another. Broadly, the distortion correction lens 60 is configured so as to be operable or co-operable with the lens 40*a* of the digital camera 40 for modifying the reflected light path 27 so as to correct, cure, or remedy one or more optical distortion effects.

By way of brief explanation, traditional lens design requires compound lenses working in combination to correct distortions and optical aberrations such as chromatic aberrations, 'barrel' distortions and 'pin cushioning'. Distortions and aberrations typically arise from the spherical structure of the lenses. To reduce the chromatic and shape distortions, lens designers require precision tooling to shape aspherical lenses.

With reference again to FIGS. 3, 4, and 5, the preferred lens 40*a* operable with the digital camera 40 is one referred to as a liquid lens which has similar properties to an aspherical lens. In the context of the principles described herein, the term 'liquid lens' is a reference to a lens formed using the natural shape of liquid droplets. Lenses of this type have been found to allow a single lens element to replace complex lens design for small microscopy cameras such as pin-hole cameras. Liquid lens technology is relatively new and currently applied in the technical area of microscopy. The inventor of the presently described technology has discovered that advantage can be obtained in applying certain optical properties of liquid lens technology in the present technical area involving close proximity imaging of skin sites using portable devices for realising similar image clarity/quality usually achieved in microscopic.

Figure 14:
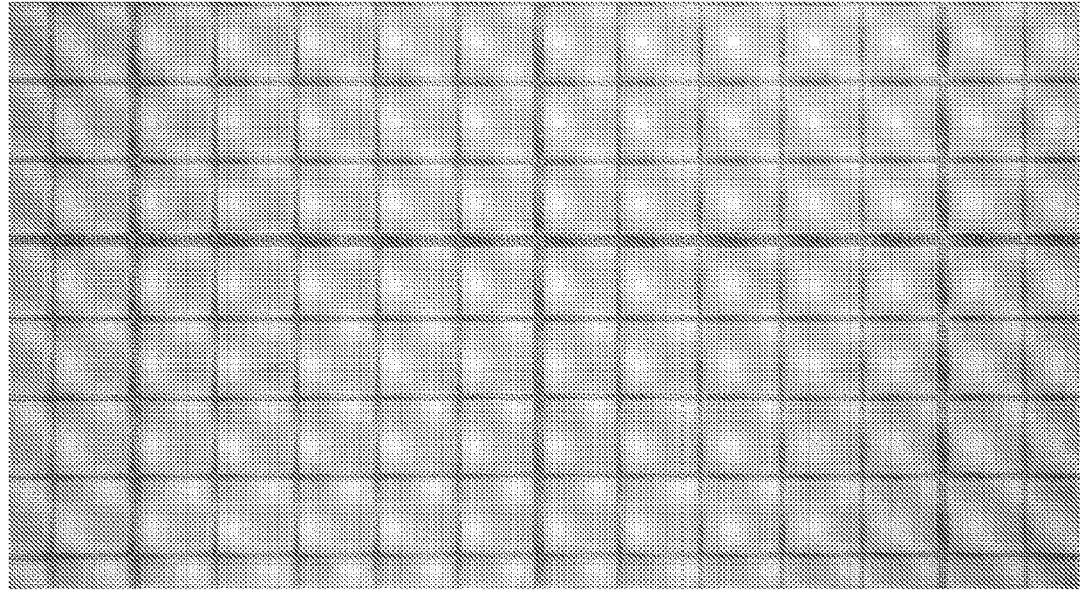
FIG. 14 shows an example image of 1 mm grid graph paper demonstrating the effectiveness of one embodiment of the optical arrangement described herein, in which all lines of the grid are shown straight without visible distortion being noticeable.

By shifting a liquid lens' focal distance away from a camera sensor, the result is close to microscopy quality, but suffers the 'fish-eye' effect or very heavy 'barrel' distortion. The barrel distortion can typically result in misdiagnosis in dermoscopy because the shape of a mole or skin condition can become distorted. The developers of the presently described technology have discovered advantage in that by placing a second aspherical achromatic lens (the distortion correction lens 60) in front of the liquid lens 40*a* (in the reflected light path 27) it is possible to induce a 'pin-cushion' effect which may reduce or cancel out the fish-eye/barrel distortion of the liquid lens 40*a*. The liquid lens 40*a* is required to be unfocused to compensate the additional focal length of the second (or distortion correction) lens 60. The final result is a generally very low distortion skin imaging system now suitable for dermascopy. Reference is made to FIG. 14 which shows an example image of 1 mm grid graph paper demonstrating the effectiveness of the optical arrangement described herein, in which all lines of the grid are shown straight without any visible distortion being noticeable.

With reference to FIG. 3, the embodiment of the optical arrangement used in the device 10 comprises a first polariser 70 (e.g., a linear polarisation filter element or member) arranged in the radiated light path 25 between the light emitting and dispersing means 30 and the skin site 18. The optical arrangement of the device 10 further comprises a second polariser 80 (e.g., a linear polarisation filter element or member) arranged in the reflected light path 27 between the skin site 18 and the digital camera 40. For the embodiment shown, the second polariser 80 is arranged in the reflected light path 27 between the distortion correction lens 60 and the digital camera 40. With reference to FIG. 3, the first polariser 70 is of flat/planar disk like form with a central aperture 70*a* provided so as to allow light reflected from the skin site 18 to reach the digital camera 40. The second polariser 80 is also of flat/planar disk like form but without a central aperture.

In one form (embodied in the device 10), the second polariser 80 is arranged so as to polarise light in an orientation that is substantially perpendicular to an orientation that the first polariser 70 polarises light. The utilisation of a pair of opposing polarising elements (70, 80) arranged operable in this manner benefits the quality of the captured image as the cross-polarisation reduces the amount of light that is directly reflected from the skin surface, thus allowing for the sub-surface details to be observed more clearly. Reflected light that has linear polarisation can be filtered out by the second polariser (80). In operation with the illumination arrangement, when the light is of a single or uniform angle engaging or entering the skin site 18, less dispersion (light distribution or spread) occurs sub-surface after entering the skin. As such, the second polariser 80 will tend to filter out most of the light reflected from the skin site 18. With the reflected scattered or diffused light received by the skin, there is more dispersion (light distribution or spread) after entering the skin and therefore the sub-surface structure becomes brighter as a larger scope of light reflected from the skin site avoids the effect of the second polariser 80.

Figure 13A:
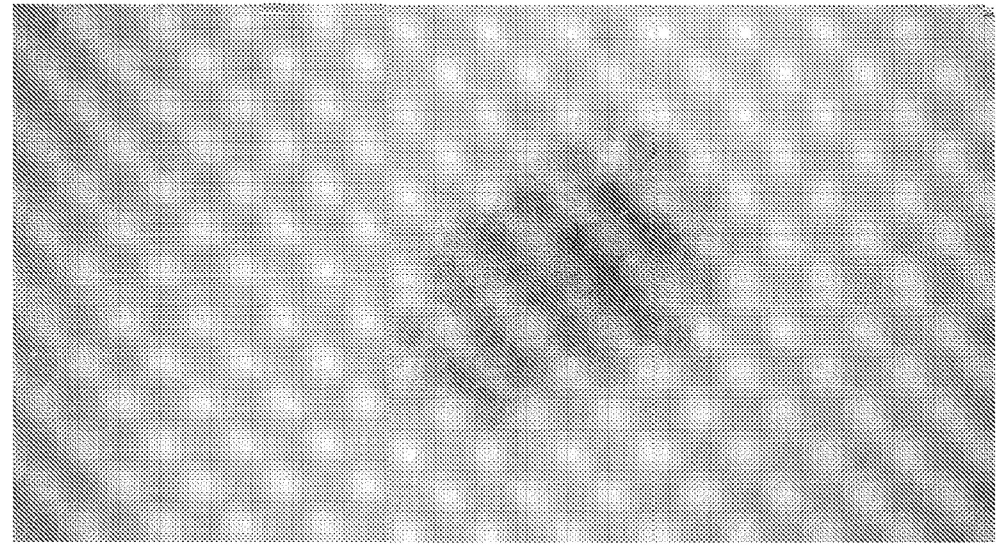
FIG. 13A shows an example of an image of a skin site without cross-polarisation, showing reflection from the oily surface (for the case shown) of the skin being seen.
Figure 13B:
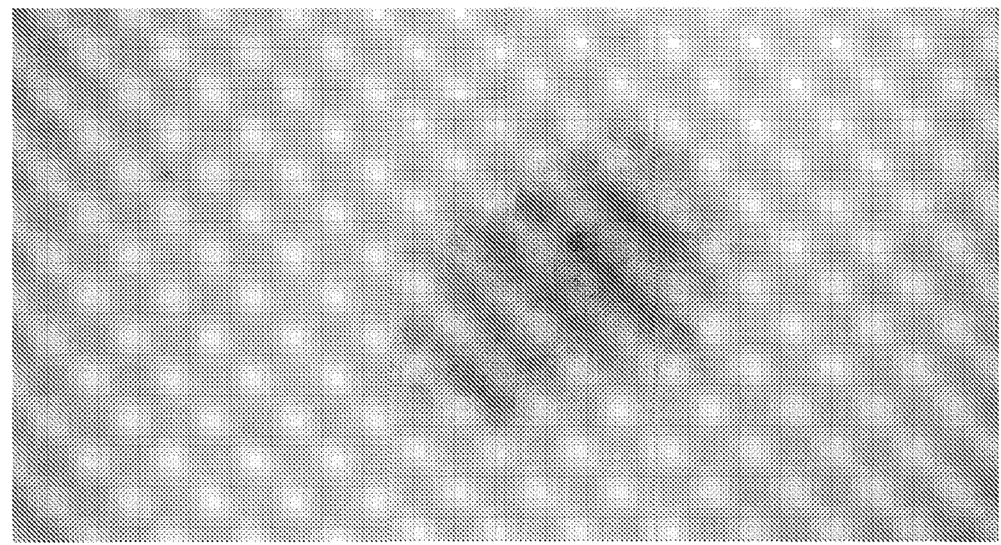
FIG. 13B shows the same example skin site shown in FIG. 13A, but with cross-polarisation enabled, where the reflection of the oily surface is filtered out.

With reference to FIGS. 3, 5 and 13, and as noted above, the first polariser 70 and the second polariser 80 are arranged or configured so as to provide the device 10 with a cross polarisation filter arrangement. As shown in FIG. 3 the first polariser 70 (a relatively larger dimensioned component as compared the second polariser 80) is placed in front of the annular arrangement of the light emitting elements 32 and the reflective mesh (34) of the light emitting and dispersing module 30 (as described below). In this manner, the first polariser 70 is arranged in the radiated light path 25 between the light emitting and dispersing module 30 and the skin site 18. The second polariser 80 (a relatively smaller dimensioned component as compared the first polariser 70) is arranged in the reflected light path 27 between the distortion correction lens 60 and the digital camera 40. The second polariser 80 operates to polarise light in an orientation generally perpendicular to an orientation that the first polariser 70 operates to polarise light (thereby enabling the cross-polarisation functionality). The first 70 and second 80 polarisers are linear polarisers with their polarising planes aligned at about 90° to each other (see the lower inset image in FIG. 3 showing the 90° alignment between the polarising planes of the first, second polarisers). The LED light going through the first polariser 70 will be polarised at one plane only. When the light penetrates into the skin, the polariser plane changes in angle and when reflected back into the digital camera 40, only light rays with the same plane will be seen by the camera. Any reflection from the outer layer of the skin site 18 will be cut out by the second polariser 80. Reference is made to FIG. 13A and FIG. 13B: FIG. 13A shows an example of an image of a skin site without cross-polarisation, showing reflection from the oily (for the case shown) surface of the skin being seen, and FIG. 13B shows the same example skin site shown in FIG. 13A, but with cross-polarisation enabled, where the reflection of the oily surface is filtered out.

Figure 2:
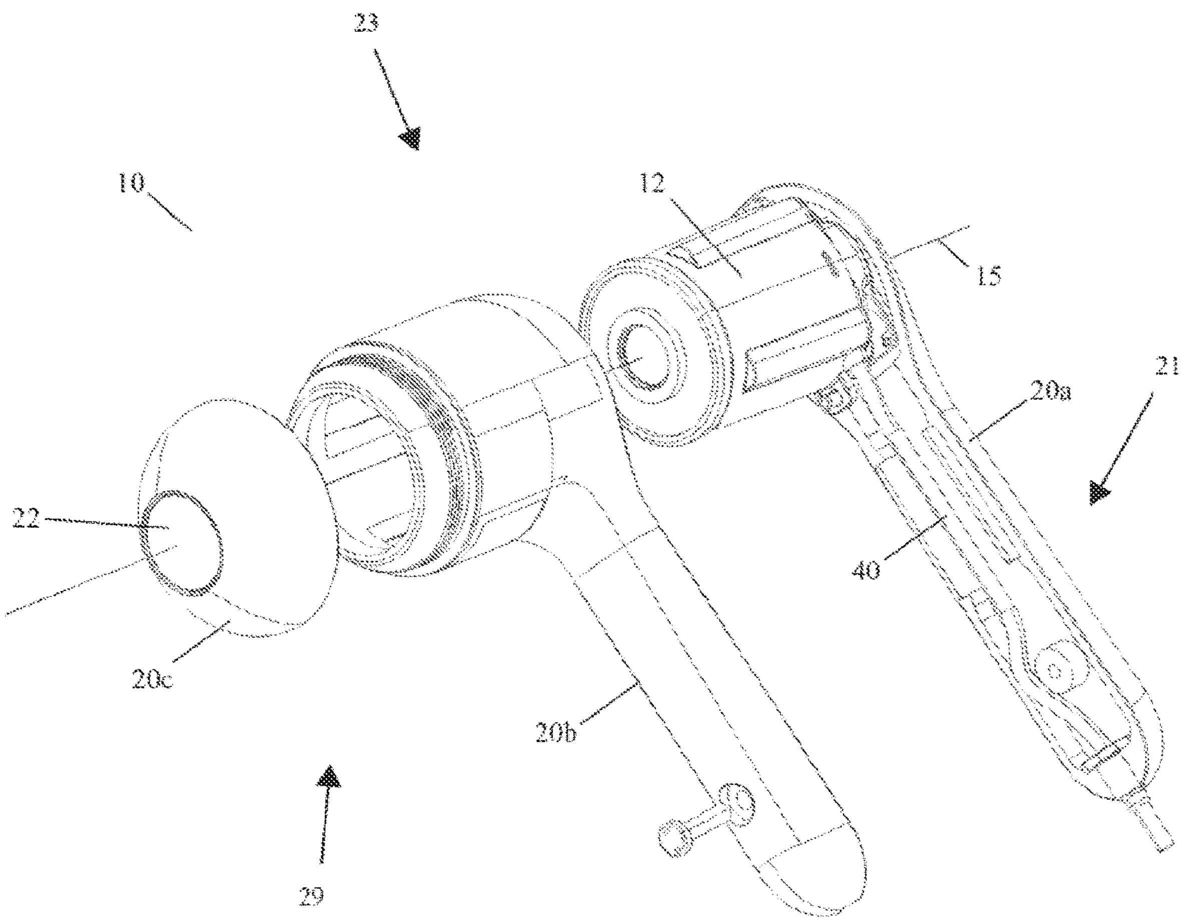
FIG. 2 is an exploded view of the embodiment of the device depicted in FIG. 1.

With reference to FIGS. 1, 2, and 4, the housing 20 is constructed from three components: a back housing component 20*a*, a front housing component 20*b* and a head housing piece 20*c*. The housing 20 is configured so as to be substantially dustproof and waterproof so as to prevent (or mitigate against) damage to the internal components and to maintain a consistent image capturing environment.

Embodiments of devices embodying the principles described herein may incorporate a handle portion for manual operation or a frame/support structure for static operation. In the form described herein, and with reference to FIG. 2 the housing 20 has a handle portion at a proximal end 21 of the device 10, and substantially cylindrical head at a distal end 23 of the device 10 which contains a component module 12. On one end of the substantially cylindrical head is a truncated hemisphere/hemispherical shaped portion with the substantially planar plate 22 of transparent plastic or glass material aligned substantially perpendicular to and centred on or relative to the central axis 15 at the most distal end 29. In use, the planar plate 22 contacts with the skin site 18, serving to generally flatten the area.

With reference to FIG. 2, a component module 12 is located within the housing 20, within the head of the device 10 and centred on or substantially concentric with the central axis 15. With reference also to FIG. 3, the component module 12 comprises: the light emitting and dispersing module 30, the digital camera 40, the distortion correction lens 60, the first polariser 70, and the second polariser 80. The light emitting and dispersing module 30, the digital camera 40, the distortion correction lens 60, the first polariser 70, and the second polariser 80 are all positioned so as to be substantially centred on or substantially concentric with the central axis 15.

In use, and with reference to FIG. 5, light is radiated generally from the light emitting and dispersing module 30 to the skin site 18 in the radiated light path 25, having a first component (25-Y) being diffused/dispersed/scattered for projection on to the skin site, and a second component (25-X) being projected directly on to the skin site. Light is reflected from the skin site 18 to the digital camera 40 in the reflected light path 27. The reflected light path 27 traverses the central axis 15 and passes through a central region of the light emitting and dispersing module 30 via aperture 72 formed in the body of the light emitting and dispersing module. The body of the light emitting and dispersing module 30 is, as described below, provided in the form of a printed circuit board (shown in FIG. 3).

As noted above, the distortion correction lens 60 is arranged in the reflected light path 27 between the skin site 18 and the digital camera 40. With reference to FIG. 3 and FIG. 5, the distortion correction lens 60 is provided in the form of a compound lens (fabricated by Edmund Optics) comprised of two optical lenses 60*a*, 60*b* fused together having respective densities different from one another. In this manner, the optical effect causes the resulting compound lens 60 to exhibit 'pin cushion' properties, the optical advantage of which operates to counteract, to the extent possible, the spherical 'barrel' distortion resulting from the liquid lens 40*a* used with the (high-resolution) digital camera 40. See FIG. 14 showing an example image (of a grid) demonstrating the effectiveness of the optical arrangement described herein.

Figure 12:
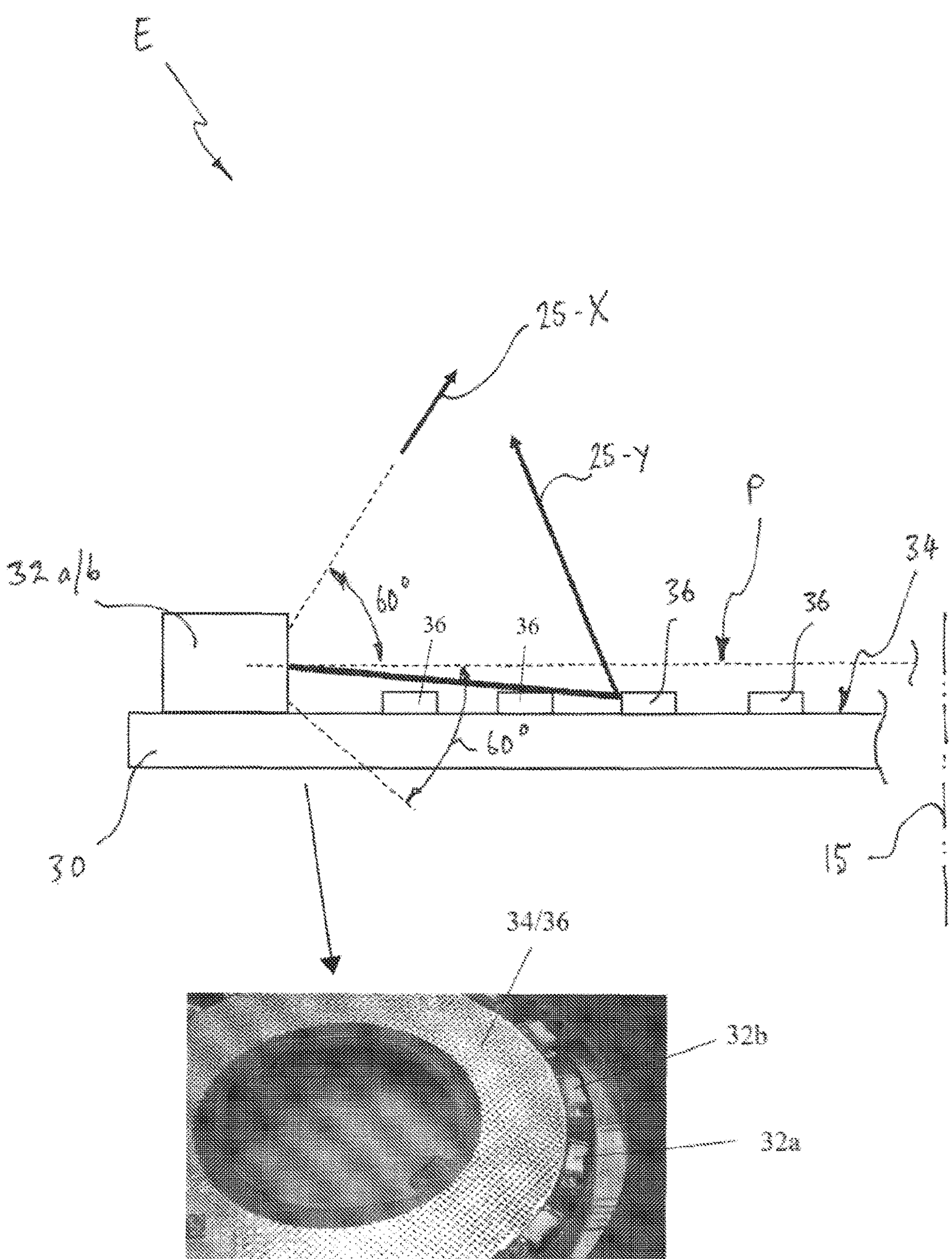
FIG. 12 is a cross-sectional detail view of region E shown in FIG. 5, and including a lower inset image showing the metallic hatch pattern of the reflective surface portion (34).

With reference to FIGS. 3, 4, 5, and 12, the light emitting and dispersing module 30 is provided in the form of a printed circuit board having a body shaped substantially that of a planar or flat annular disk like form/profile, and which is oriented, in use, so as to align substantially perpendicular to/with the central axis 15 of the device 10. The body of the light emitting and dispersing module 30 further comprises the generally circular shaped aperture 72 (as shown in FIG. 3) which is aligned so as to be substantially concentric with the central axis 15 for enabling light reflected (27) from the skin site 18 to reach the digital camera 40. A surface of a portion 34 of the body of the light emitting and dispersing module 30 is arranged so as to face the skin site 18, and is configured so as to be reflective and, in the embodiment shown, comprises or is provided with embossments or raised formations/features which renders the general form of the surface portion 34 in a substantially uneven manner. For the embodiment of the device 10 described herein, and as shown in FIG. 5 and FIG. 12, the uneven nature of the surface portion 34 is provided by way of a regular pattern of raised formations provided by way of a metallic mesh having hatchings (see FIG. 12, where the lower inset image shows the metallic hatch pattern of the reflective surface portion 34) providing multiple ridges 36. However, it will be appreciated that the uneven nature of the surface portion 34 could be achieved in a number of ways, including, for example, an appropriate substrate or applied coating (e.g., a reflective coating) exemplifying an appropriate patterned texture or hatchings operable for reflecting light received thereby in a manner which serves to diffuse, disperse or scatter received light away from the surface portion 34 for projection on to the skin site 18.

The light emitting and dispersing module 30 comprises a plurality of light emitting elements provided in the form of light emitting diodes (LEDs) operable for emitting light for illuminating the skin site 18. With reference to FIGS. 3, 4, and 5, a plurality of LEDs 32*a*, 32*a* (collectively, LEDs 32) are arranged equidistant to each other generally adjacent (at or near) the perimeter or circumference of the planar annular disk like form/profile of the printed circuit board of the light emitting and dispersing module 30. As will be described below, and as shown in FIG. 3, the plurality of LEDs 32 are comprised of two sets: a first set of LEDs 32*a*, and a second set of LEDs 32*b*. In the arrangement shown in FIG. 3, both sets of LEDs 32*a*, 32*b* are arranged so as to be positioned in an alternating or interleaving manner about the annular form at about the same radius outward from a centre of the planar annular disk like form/profile of the printed circuit board of the light emitting and dispersing module 30. As shown in FIG. 3, a light emitting element of one of the sets of light emitting elements (for example, LED 32*b*) is positioned adjacent or intermediate/between light emitting element(s) (e.g., LEDs 32*a*) of the alternate set of light emitting elements. In this manner, a first LED ring is formed by way of the LEDs 32*a*, and a second LED ring is formed by way of the LEDs 32*b*.

Each of the LED rings can be configured so as to be selectively operable (e.g., by way of a control/activation means on the device, or via an external electronic device associated with the device). In the form shown, the device 10 comprises appropriate electronic circuitry and processing capability for operation as the skilled reader would understand. Each LED ring is controllable (by respective controllers) using a respective light emitting diode driver module (each provided in the form of LT3593 driver modules) for controlling the degree of brightness/intensity of the LEDs of each respective LED ring as might be desired during a skin examination by an examining clinician. The intensities of the LEDs 32 are controlled or controllable by software to allow a variable combination of filtered (polarised) and unfiltered (unpolarised) light to reach the surface of the skin site 18 (using apertures 71, as described below). Light reflected from the surface of the skin site 18 is then filtered by the second polariser 80 (in the reflected light path 27) before entering the digital camera 40. By way of these controlled or controllable intensities of the LEDs 32, the structures in the skin can be illuminated in all manner and hence produces a much clearer or enhanced image for capture by the digital camera 40 or for manual visual inspection. In this manner, a varying degree of brightness/intensity of emitted light from each LED ring, in combination with the apertures 71, can be sought enabling clinicians to observe certain conditions which can be difficult to identify using either of the LED rings alone. For the present embodiment of the device 10, the LEDs 32 used are controllable so that each offers 32 available levels of intensity.

The LEDs 32 are oriented so as to emit light on to the surface portion 34. With reference to FIGS. 3, 5, and 12, and as foreshadowed above, the LEDs 32 are orientated so that their full scope of light emission does not shine directly onto the skin surface of the object. In this manner, each of the LEDs 32 are orientated or angled at about 90° with respect to a plane in which the reflective ridge formations 36 of the reflective surface portion 34 (see FIGS. 3 and 12) aligns so that a portion of the emitted light meets or makes contact with the reflective surface portion 34 so as to be received by the ridges 36, which meeting/contact is operable for producing the desired light diffusion/dispersion/scattering effect before reflecting the scattered/diffused/dispersed light for projection toward and/or onto the surface of the skin site 18 reminiscent of what is sought to be achieved using a technique sometimes referred to as 'bounce flash' photography. With regard to FIG. 12, the LEDs 32 are configured so as to have or provide a scope of emitted light having about a 120° dispersion angle on a plane that is aligned substantially perpendicular to the surface portion 34 (see FIG. 12 showing the scope of the dispersion of the light emitted from the LEDs 32 about an axis P that aligns mid-way between the edges of the 120° scope of dispersion from the LED 32 and which is substantially parallel with the skin site 18). The positioning of the LEDs 32 in this manner ensures that a portion of the scope of the emitted light shines or radiates towards the surface portion 34 and another portion of the scope of the emitted light shines/radiates toward the skin site 18. Thus, as the LEDs 32 have a generally wide illumination angle of about 120°, a portion of light emitted or radiated from the LEDs 32 is also able to shine onto the surface of the skin site 18. It has been found that this combined illumination (involving the light beams 25-X and 25-Y) can also assist in producing a 'soft' or 'softened' reflective illumination (for example, being of a generally shadowless nature) rather than exhibiting what can be referred to as a 'hard' illumination (with more pronounced shadow features).

As foreshadowed above, the cross-polarisation effect employed in the device 10 may be adjusted and or adjustable during a skin examination. As shown in FIG. 3, the first polariser 70 is configured with a number of laser cut apertures 71 regularly spaced about its annular planar form (concentric with the central axis 15). Generally, the apertures 71 operate to allow light emitted from the LEDs 32 to avoid being polarised by the first polariser 70 prior to reaching the skin site 18. The size and placement of the apertures 71 with respect to the LEDs 32 is considered to enable about one half of the emitted light to be filtered by the first polariser 70, and about one half of the emitted light to avoid being subject to the polarising effect of the first polariser 70. As noted above, the first 70 and second 80 polarisers are linear polarisers and aligned relative to reach so that their polarising planes are at about 90° to each other. As such, the LED light emitted through the apertures 71 will be polarised at one plane only by way of the second polariser 80.

When the light penetrates into the skin of the skin site 18, the polariser plane changes in angle and when reflected back toward the digital camera 40, only the reflected light with the same plane will be seen by the camera. Any reflection from the outer layer of the skin will be cut out by the second polariser 80. In this manner, projection of emitted light of a fully polarised nature via the first polariser 70 enables a mode of operation in which an examination of a generally dry skin site to be undertaken ("dry" method of skin examination). Furthermore, projection of emitted light of a fully unpolarised nature via the apertures 71 enables a mode of operation in which an examination of the skin site 18 can be undertaken where an appropriate fluid or oil has been applied ("wet" method of skin examination).

As again seen in FIG. 3, each aperture 71 is positioned so as to correspond with a LED 32*b* of the second LED ring. As such, light emitted from LEDs 32*b* of the second LED ring (either directly or on reflection from the surface portion 34) passing through a respective corresponding aperture 71 of the first polariser 70 will not be polarised prior to reaching the skin site 18. Similarly, it will be seen in FIG. 3 that the majority of the light emitted from LEDs 32*a* of the second LED ring (either directly or on reflection from the surface portion 34) will meet the first polariser 70 and be subject to its polarising effect prior to reaching the skin site 18. In this manner, the relative positioning of a LED 32*b* and its corresponding aperture 71, and the variable nature of the brightness/intensities of the light emitted from one or both of the LED rings 32*a*, 32*b* (by way of their respective control circuitries), operates to enable a degree of control over the quantity and/or intensity of polarised or unpolarised light that reaches the surface of the skin site 18. In this manner, a varying degree of brightness/intensity of emitted light from each LED ring can be sought enabling clinicians to observe certain conditions which can be difficult to identify using either of the LED rings alone.

An inner or interior surface 24 (or portions thereof) of the housing 20*c* adjacent the plate 22 is configured so as to be reflective of light received thereby. This increases the quantity of diffused/dispersed/scattered light 25 which can be projected by the device 10, and thus aids in the efficiency of the device 10. With reference again to FIG. 5, light beams 25-X and 25-Y are shown to be emitted from the LEDs 32 through the plate 22. As seen, light beam 25-X travels directly from the LEDs 32 and light beam 25-Y reflects or 'bounces' off of a portion of the inner or interior surface 24 of the housing 20*c* following reflection from the reflective/dispersing/scattering surface portion 34 of the light emitting and dispersing module 30.

The device 10 comprises a power supply module configured operable for supplying or distribution electrical energy or power to any of the on-board components requiring electrical power. The power supply module may be external and/or internal. For the embodiment shown, the power supply module is on-board the device 10 and configured operable for providing power for light emission, image receiving/capturing, and any control systems the device 10 may have.

In various forms, the power supply module may comprise or be arranged operable with a power receiving module configured for receiving electrical energy or power from a source of electrical energy or power (e.g., mains power source, battery power source) and which may be external of the device or internal/on-board the device for supplying or distributing electrical energy/power to any of the on-board components carried by the device 10 as required for operation.

In the form shown, the device 10 is configured connectable with an electronic device, such as for example, an external electronic device such as, for example, a laptop or desktop computer, by way of a cable connection 50 (for example, a USB cable, but it will be appreciated that any suitably configured cable could be employed). The cable connection 50 transfers imaging data from the device 10 to the external electronic device (e.g., computer). Additionally, power is supplied to the device 10 via the cable connection 50 from the external electronic device (e.g., laptop/desktop computer), and or which may charge an on-board battery module if present. In one mode of operation, for example, the LEDs 32 are automatically turned on when the device 10 is supplied with power.

In some embodiments, devices (10) arranged in accordance with the principles described herein may comprise a local or on-board power source, such as for example, a battery module or similar.

In alternative embodiments, devices 10 may be configured so that the relevant image receiving/capturing module (40) used may accommodate manual or in-situ real-time observation of the skin site, similar to, for example, a microscope, rather than purely relying on digital or analogue image capturing.

Devices (10) arranged in accordance with the principles described herein may be arranged so as to be capable of being placed in wireless communication with a suitable electronic device (portable or otherwise) for operation and/or signal/data transfer/communication.

In one form, software hosted by the relevantly connected electronic device communicates (via wired or wireless arrangements) with an internal micro-controller inside the digital camera 40 and which is configured operable for controlling the two independent (boost) light emitting diode driver modules (each provided in the form of LT3593 driver modules) that operate respective LED (32*a,b*) rings as described above. In this manner, a varying degree of brightness/intensity of emitted light (for the embodiment shown, 32 levels of brightness/intensity are provided for) can be sought enabling clinicians to observe certain conditions which can be difficult to assess/identify using either of the LED rings alone.

The device 10 comprises appropriate electronic circuitry for operation which comprises a processor enabled by way of a suitable processor module. The processor module may be configured so as to be capable of receiving one or more signals (for example, from an electronic device (portable or otherwise, and which could be operable by way of a consumer or having been suitably programmed by a consumer) such as a control station, a tablet device, mobile phone, desktop computer, remote transmitting device and the like. A signal could also be transmitted by the electronic device causing or implementing any type of operational event to occur. Thus, the processor module could be operable with a communication module (not shown) so that control signals/commands can be received from the relevantly associated/connected electronic device. Such an electronic device could communicate with the processor module using sufficiently equipped near field communication (NFC). Any other wireless protocol could also be used. The processor module may be configured for controlling or managing all operations of the device 10 during use, independently or with input from the relevant electronic device.

The device 10 further comprises a control means in the form of a button 90 on the back of the head of the housing 20 that when activated signals the device 10 to capture an image. When depressed, the button 90 signals the digital camera 40 to take an image. Such a control means may comprise a touchpad (or similar interface means) that when activated signals the device 10 to capture an image. As noted above, the device 10 may be configured so that the image capturing device means used may accommodate manual observation of the relevant target skin site (for example, similar to a microscope) rather than purely relying on digital or analogue image capturing and which control means (e.g., button, touchpad) is operable for enabling manual observation.

The FIGS. depict additional structural features of the housing 20 and the component module 12, such as gaskets, screw thread and fastening points that would be within the consideration of a person skilled in the art.

In accordance with another aspect there is provided a method of examining skin using embodiments of devices embodying the principles described herein. Broadly, one such method involves: selecting a target skin site (18), positioning an embodiment of such a device (10) such that the substantially planar plate (22) contacts the skin site (18), activating the device (10) so as to emit light within the device whereby a significant amount of light is diffused/dispersed or scattered within the device, and projecting the light (25) on to the skin site (18), whereby light reflected from the skin site (18) travels the reflected light path (27) to the image capturing module (40) for capture of the image data.

Most of the light is diffusely reflected at the stratum corneum. Some light is reflected by deeper parts of the epidermis. Further, some light is typically absorbed.

Light may be polarised by a first polariser (70) prior to being projected on to the skin site (18).

Light in the reflected light path (27) may pass through a distortion correction lens (60) prior to reaching the image capturing means (40).

Light in the reflected light (27) path may be polarised by a second polariser (80) prior to reaching the image capturing means (40).

The image capturing means (40) may transmit the image data to an external computer or electronic device.

The image data may be recorded, reviewed, compared and monitored for changes over time. These actions may be performed using software by the external computer.

The image data may be modified using software. This may clear up defects or aberrations in an image, identify areas of note, and/or perform other functions that would benefit a diagnosis.

FIGS. 6 to 11 are comparison images of a range of skin conditions between images taken with a device in accordance with the technology described in Australian patent AU 199538975, and a device (10) arranged substantially in accordance with one embodiment of the present invention respectively. Comparison images were taken of the same patient on the same day.

Figure 6:
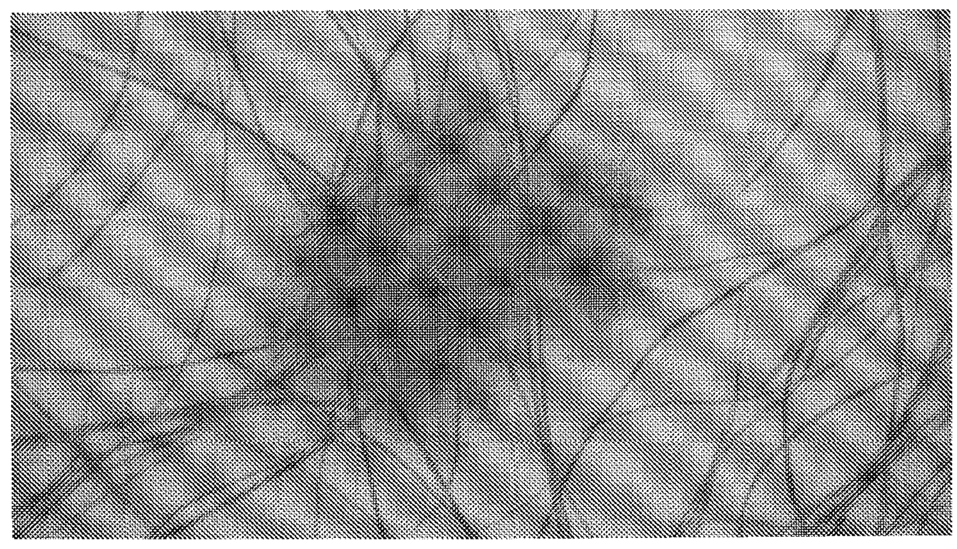
FIG. 6 is an image taken of an Irritated mildly Dysplastic Junctional Melanocytic Naevus taken with a device in accordance with Australian patent AU 199538975.
Figure 7:
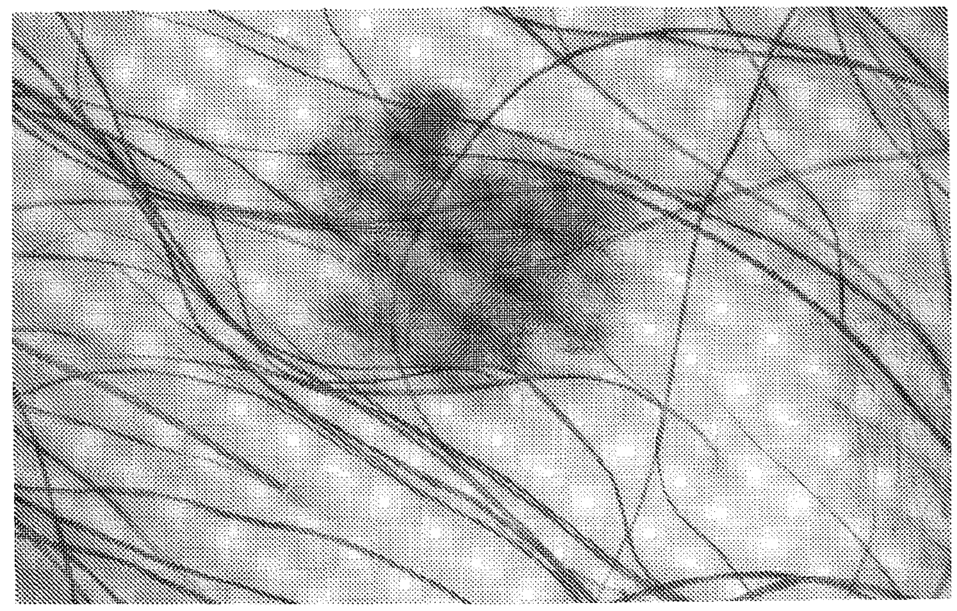
FIG. 7 is an image taken of an Irritated mildly Dysplastic Junctional Melanocytic Naevus taken with a device in accordance with the present invention.

FIGS. 6 and 7 are images taken of an Irritated mildly Dysplastic Junctional Melanocytic Naevus. The image, taken by a device (10) arranged substantially in accordance with one embodiment of the present invention, is capable of showing where the hair enters and a more distinct net like structure.

Figure 8:
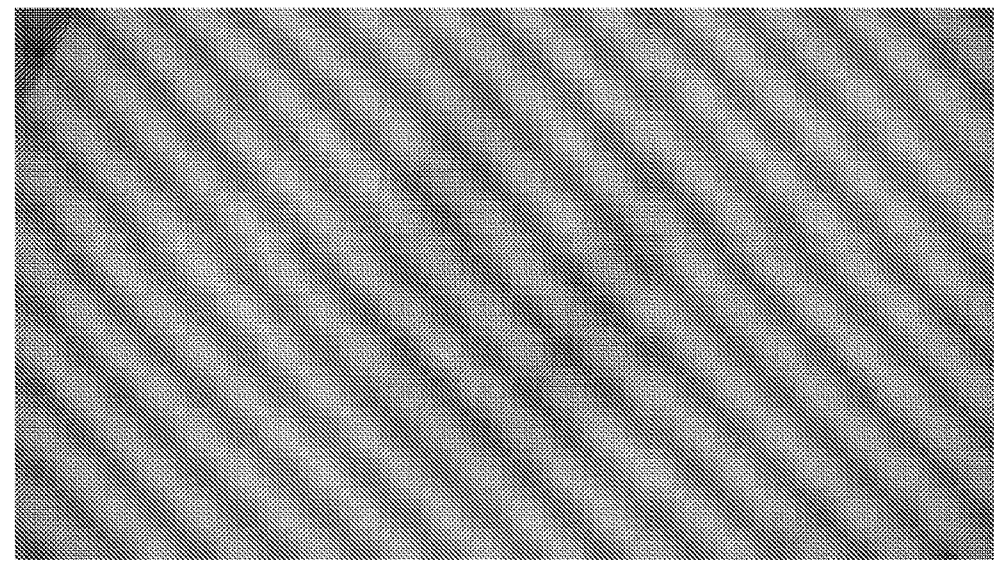
FIG. 8 is an image taken of a Nodular Basal Cell Carcinoma taken with a device in accordance with Australian patent AU 199538975.
Figure 9:
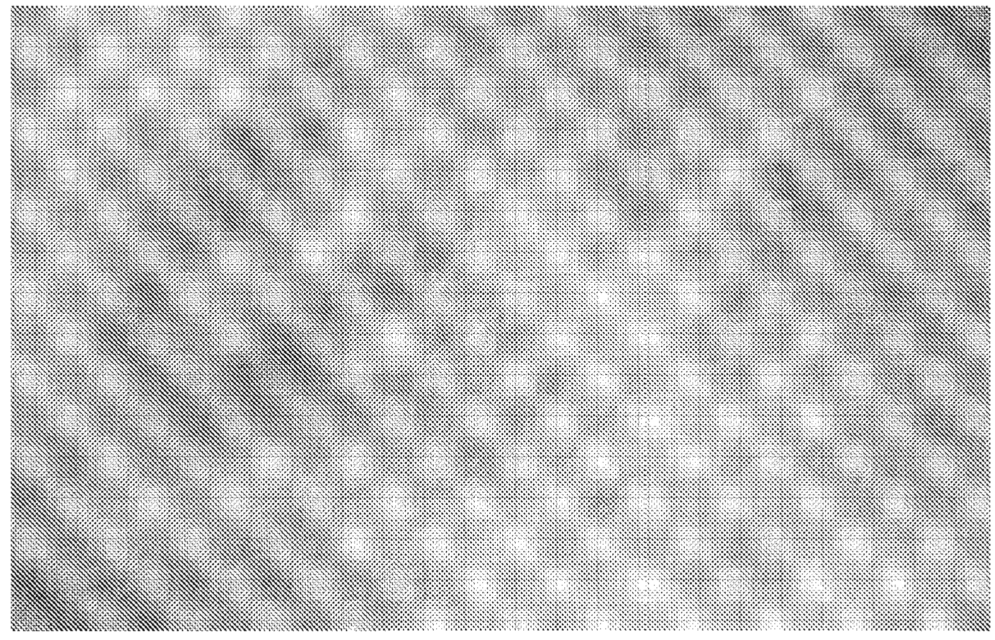
FIG. 9 is an image taken of a Nodular Basal Cell Carcinoma with a device in accordance with the present invention.

FIGS. 8 and 9 are images taken of a Nodular Basal Cell Carcinoma (BCC). In the image, taken by an embodiment of a device (10) arranged substantially in accordance with one embodiment of the present invention, more blood vessels can be identified underneath the skin surface and the distinct BCC structure can be seen more clearly.

Figure 10:
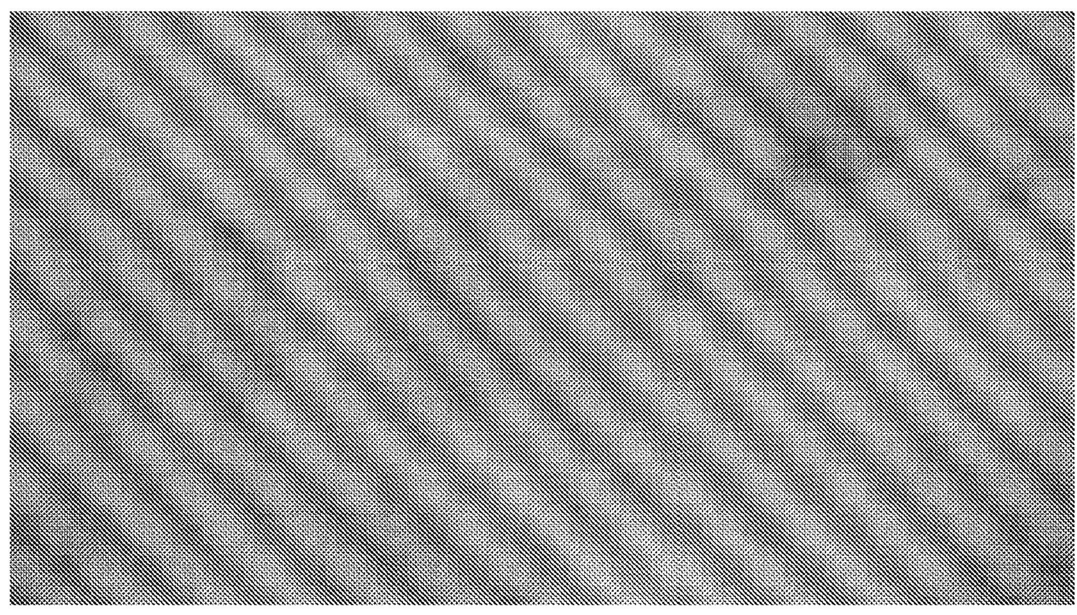
FIG. 10 is an image taken of a Basal Cell Carcinoma taken with a device in accordance with Australian patent AU 199538975.
Figure 11:
FIG. 11 is an image taken of a Basal Cell Carcinoma with a device in accordance with the present invention.

FIGS. 10 and 11 is an image taken of a Basal Cell Carcinoma. The image, taken by an embodiment of a device (10) arranged substantially in accordance with one embodiment of the present invention, shows clearer blood vessels and structures underneath the skin.

Further methods exemplifying aspects of the principles described herein may also other advantage/utility. According to a further aspect, methods for illuminating a skin site (18) in the examination of the skin site, may, broadly, involve, at least in one example embodiment: configuring a reflector means or module so as to have a reflecting portion (34) configured operable for reflecting light received thereby. Such example embodiment may further involve configuring a light emitting means or module (32) so as to be arranged between the reflector means or module and the skin site (18), and configuring the light emitting means with the reflector means or module so that a portion of light emitted from the light emitting means or module meets or makes contact with the reflecting portion (34). Such example embodiment may further involve configuring the reflecting portion (34) of the reflector means or module so that the meeting or contact between the portion of light emitted from the light emitting means or module (32) and the reflecting portion is operable so as to promote scattering or diffusion of light reflected from the reflecting portion for projection on to the skin site (18) for increasing the variability or non-uniformity of incidence of the reflected scattered/diffused light received across the skin site.

In another aspect, methods for an imaging for a device (10) operable for use in the examination of a skin site (18) may other advantage/utility. In one such example, the relevant device (10) may be arranged operable with an illumination means or module (30) arranged operable for illuminating the skin site (18), and an imaging means or module (40) operably associated with a lens (40*a*) by way of which light is received by the imaging means or module (40). The illumination means or module (30) may be operable for illuminating the skin site (18) so that light is reflected therefrom toward the imaging means or module (40) in a reflected light path (27). Broadly, in one embodiment, a relevant imaging method may involve configuring a further lens (60) so as to be operable for modifying a light path received thereby so as to be operable or co-operable with the lens (40*a*) of the imaging means or module (40) so that the reflected light path (27) is subject to a modification operating to substantially correct for one or more optical distortion effects prior to reaching the imaging means or module (40). Such example embodiment may further involve arranging the further lens (60) so as to be in the reflected light path (27) between the skin site (18) and the lens (40*a*) of the imaging means or module (40). Such example embodiment may further involve causing the skin site (18) to be illuminated by way of the illumination means or module (30) so that light is reflected (27) from the skin site (18) toward the imaging means or module (40) in the reflected light path (27).

Modifications and variations as would be apparent to a skilled addressee are deemed to be within the scope of the present invention.

The invention claimed is:

1. An optical arrangement for use with a device operable for use in examination of a skin site, the device having or arranged operable with an illumination arrangement configured operable for illuminating the skin site and an imaging module, the optical arrangement comprising:

a lens of a liquid lens type arranged in operable association with the imaging module, and a distortion correction lens, the lens and the distortion correction lens being arranged so as to share an axis of the optical arrangement which aligns generally normal with the skin site when the optical arrangement is provided in an in-use orientation, the illumination arrangement with which the optical arrangement is operable comprises a plurality of light emitting elements at or near a perimeter of the illumination arrangement, the illumination arrangement further comprising a reflective surface portion configured to be oriented so as to face the skin site so as to be in substantial parallel relation therewith during use of the optical arrangement or the device, whereby the light emitting elements are oriented relative to the reflective surface portion so that each provide a scope of emitted light that disperses about a respective axis, the respective axis is generally parallel with the reflective surface portion, on to a plane that intersects with or passes through the axis of the optical arrangement and which plane is aligned generally perpendicular with the reflective surface portion so as to enable emission of a portion of the scope of emitted light on to the reflective surface portion, and wherein the reflective surface portion is configured operable so as to promote scattering or diffusion of light received from the light emitting elements for reflection from the reflective surface portion for projection on to the skin site for increasing variability of incidence of the reflected scattered or diffused light received across the skin site, and wherein the optical arrangement is configured operable so that, in use, on illumination by way of the illumination arrangement light is reflected from the skin site toward the imaging module in a reflected light path, and wherein the distortion correction lens is configured to be arranged in the reflected light path between the skin site and the liquid lens.

2. An optical arrangement according to claim 1, further comprising a first polariser configured to be arranged in a radiated light path between the illumination arrangement and the skin site.

3. An optical arrangement according to claim 1, further comprising a second polariser configured to be arranged in the reflected light path between the skin site and the imaging module.

4. An optical arrangement according to claim 3, wherein the second polariser is arranged in the reflected light path between the distortion correction lens and the imaging module.

5. An optical arrangement according to claim 3, wherein the second polariser polarises light in an orientation substantially perpendicular to an orientation that a first polariser polarises light.

6. A device for examination of a skin site comprising the optical arrangement according to claim 1.

7. A device for examination of a skin site comprising:

a housing, an illumination arrangement arranged within the housing, the illumination arrangement comprises a plurality of light emitting elements at or near a perimeter of the illumination arrangement, the illumination arrangement further comprising a reflective surface portion configured to be oriented so as to face the skin site so as to be in substantial parallel relation therewith during use of the device, whereby the light emitting elements are oriented relative to the reflective surface portion so that each provide a scope of emitted light that disperses about a respective axis, the respective axis is generally parallel with the reflective surface portion, on to a plane that intersects with or passes through an axis of the device and which plane is aligned generally perpendicular with the reflective surface portion so as to enable emission of a portion of the scope of emitted light on to the reflective surface portion, and wherein the reflective surface portion is configured operable so as to promote scattering or diffusion of light received from the light emitting elements for reflection from the relative surface portion for projection on to the skin site for increasing variability of incidence of the reflected scattered or diffused light received across the skin site, an imaging module arranged within the housing, a lens of a liquid lens type arranged in operable association with the imaging module, and a distortion correction lens, the lens and the distortion correction lens being arranged so as to share the axis of the device, the axis of the device aligns generally normal with the skin site when the device is provided in an in-use orientation, wherein, in use, the device is configured operable so that:

(i) light is radiated by way of the illumination arrangement for projection on to the skin site in a radiated light path; and (ii) light is reflected from the skin site toward the imaging module in a reflected light path;

wherein the distortion correction lens is configured to be arranged in the reflected light path between the skin site and the liquid lens.

8. A device according claim 7, wherein the device further comprises a first polariser configured to be arranged in the radiated light path between the illumination arrangement and the skin site.

9. A device according to claim 8, wherein the first polariser is configured with one or more apertures for enabling a portion of light of the radiated light path to pass therethrough.

10. A device according to claim 7, wherein the device further comprises a second polariser configured to be arranged in the reflected light path between the skin site and the imaging arrangement.

11. A device according to claim 10, wherein the second polariser is arranged in the reflected light path between the distortion correction lens and the imaging module.

12. A device according to claim 10, wherein the second polariser polarises light in an orientation substantially perpendicular to an orientation that a first polariser polarises light.

13. A device according to claim 7, wherein a portion of the housing has an optical axis, and wherein the radiated and the reflected light paths are configured so as to operate generally about the optical axis.

14. A device according to claim 13, wherein:

(i) the illumination arrangement, and/or (ii) the imaging module, and/or (iii) first and/or second polariser, are arranged so as to be substantially concentric with the optical axis.

15. A device according to claim 13, wherein the illumination arrangement comprises a body having a profile reminiscent substantially in the form of a flat or planar annular disk oriented substantially perpendicular to the optical axis of the device.

16. A device according to claim 13, wherein the reflected light path traverses the optical axis and passes through a centre of the illumination arrangement.

17. A device according to claim 7, wherein the plurality of light emitting elements are arranged on at or near a perimeter of a body of the illumination arrangement.

18. A device according to claim 7, wherein the light emitting elements are arranged equidistant to each other.

19. A device according to claim 7, wherein any of the light emitting elements are configured having about a 120° dispersion angle on to the plane aligned substantially perpendicular to or with the reflective surface portion of the illumination arrangement.

20. A device according to claim 7, wherein the reflective surface portion of the illumination arrangement is configured so as to be substantially uneven or of a non-uniform nature so as to diffuse or scatter light received from the light emitting elements of the illumination arrangement away from the reflective surface portion.

21. A device according to claim 7, wherein the reflective surface portion of the illumination arrangement is configured having a generally regular pattern of embossments, protuberances or raised portions which renders the general form of the reflective surface portion in a substantially uneven or non-uniform manner.

22. A device according to claim 7, wherein an inner surface of the housing is configured so as to reflect light incident thereon.

* * * * *